(12) United States Patent
Bosua

(10) Patent No.: US 11,063,373 B1
(45) Date of Patent: Jul. 13, 2021

(54) NON-INVASIVE ANALYTE SENSOR AND SYSTEM WITH DECOUPLED TRANSMIT AND RECEIVE ANTENNAS

(71) Applicant: Know Labs, Inc., Seattle, WA (US)

(72) Inventor: Phillip Bosua, Seattle, WA (US)

(73) Assignee: KNOW LABS, INC., Seattle, WA (US)

( * ) Notice: Subject to any disclaimer, the term of this patent is extended or adjusted under 35 U.S.C. 154(b) by 0 days.

(21) Appl. No.: 17/123,932

(22) Filed: Dec. 16, 2020

Related U.S. Application Data

(60) Provisional application No. 62/951,756, filed on Dec. 20, 2019.

(51) Int. Cl.
*H01Q 21/28* (2006.01)
*H01Q 1/38* (2006.01)
(Continued)

(52) U.S. Cl.
CPC .......... *H01Q 21/28* (2013.01); *A61B 5/0507* (2013.01); *A61B 5/14532* (2013.01); *H01Q 1/38* (2013.01); *H01Q 1/521* (2013.01)

(58) Field of Classification Search
CPC .......... H01Q 21/28; H01Q 1/38; H01Q 1/521; A61B 5/0507; A61B 5/14532
See application file for complete search history.

(56) References Cited

U.S. PATENT DOCUMENTS

| | | | |
|---|---|---|---|
| 8,223,021 B2 * | 7/2012 | Goodnow | A61B 5/0022 340/572.1 |
| 9,198,607 B2 | 12/2015 | Fischer | |

(Continued)

FOREIGN PATENT DOCUMENTS

| | | |
|---|---|---|
| JP | 2012125382 | 7/2012 |
| KR | 1020160081740 | 7/2016 |

(Continued)

OTHER PUBLICATIONS

Hanna, J. et al., "Noninvasive, wearable, and tunable electromagnetic multisensing system for continuous glucose monitoring, mimicking vasculature anatomy," Science Advances, 6, eaba5320, 2020 (11 pages).

(Continued)

*Primary Examiner* — Seung H Lee
(74) *Attorney, Agent, or Firm* — Hamre, Schumann, Mueller & Larson, P.C.

(57) ABSTRACT

A non-invasive analyte sensor includes at least one transmit antenna/element that functions to transmit a transmit signal in a radio or microwave frequency range of the electromagnetic spectrum into a target containing an analyte of interest, and at least one receive antenna/element that functions to detect a response resulting from transmission of the transmit signal by the transmit antenna/element into the target. The transmit and receive antennas/elements are decoupled from one another which helps to improve the detection capability of the non-invasive analyte sensor. The decoupling between the transmit and receive antennas is achieved by using at least one intentionally fabricated configuration and/or arrangement therebetween that is sufficient to decouple the transmit antenna and the receive antenna from one another.

23 Claims, 12 Drawing Sheets

(51) Int. Cl.
*A61B 5/0507* (2021.01)
*A61B 5/145* (2006.01)
*H01Q 1/52* (2006.01)

(56) References Cited

U.S. PATENT DOCUMENTS

| | | | |
|---|---|---|---|
| 9,864,024 | B2 | 1/2018 | Vester |
| 10,149,629 | B2 | 12/2018 | Szczepaniak et al. |
| 10,478,101 | B1 | 11/2019 | Cespedes et al. |
| 10,548,503 | B2 | 2/2020 | Bosua |
| 2003/0036713 | A1 | 2/2003 | Bouton et al. |
| 2004/0065158 | A1 | 4/2004 | Schrepfer et al. |
| 2004/0127777 | A1 | 7/2004 | Ruchti et al. |
| 2004/0133086 | A1 | 7/2004 | Ciurczak et al. |
| 2009/0275814 | A1 | 11/2009 | Watanabe et al. |
| 2010/0041969 | A1 | 2/2010 | Beise |
| 2011/0028814 | A1* | 2/2011 | Petersen ............ A61B 5/6833 600/324 |
| 2014/0213870 | A1 | 7/2014 | Hsu et al. |
| 2016/0051171 | A1 | 2/2016 | Pikov et al. |
| 2017/0095667 | A1 | 4/2017 | Yakovlev et al. |
| 2018/0028824 | A1 | 2/2018 | Pivonka et al. |
| 2019/0008422 | A1 | 1/2019 | Leath et al. |
| 2019/0053741 | A1 | 2/2019 | Chaudhry |
| 2019/0104939 | A1 | 4/2019 | Costantine et al. |
| 2019/0353752 | A1 | 11/2019 | Lin et al. |
| 2019/0357800 | A1 | 11/2019 | Bosua |
| 2019/0388000 | A1 | 12/2019 | Costantine et al. |
| 2020/0057163 | A1 | 2/2020 | Bromberg |
| 2020/0146584 | A1 | 5/2020 | Bosua |
| 2020/0187791 | A1 | 6/2020 | Leabman |
| 2020/0187792 | A1 | 6/2020 | Leabman |
| 2020/0187793 | A1 | 6/2020 | Leabman |
| 2020/0187812 | A1 | 6/2020 | Leabman |
| 2020/0187813 | A1 | 6/2020 | Leabman |
| 2020/0187814 | A1 | 6/2020 | Leabman |
| 2020/0187815 | A1 | 6/2020 | Leabman |
| 2020/0187816 | A1 | 6/2020 | Leabman |
| 2020/0187817 | A1 | 6/2020 | Leabman |
| 2020/0187818 | A1 | 6/2020 | Leabman |
| 2020/0187819 | A1 | 6/2020 | Leabman |
| 2020/0187820 | A1 | 6/2020 | Leabman |
| 2020/0187836 | A1 | 6/2020 | Leabman |
| 2020/0187837 | A1 | 6/2020 | Leabman |
| 2020/0187867 | A1 | 6/2020 | Leabman |
| 2020/0191909 | A1 | 6/2020 | Leabman |
| 2020/0191932 | A1 | 6/2020 | Leabman |
| 2020/0191933 | A1 | 6/2020 | Leabman |
| 2020/0191944 | A1 | 6/2020 | Leabman |
| 2020/0191945 | A1 | 6/2020 | Leabman |
| 2020/0191947 | A1 | 6/2020 | Leabman |
| 2020/0192426 | A1 | 6/2020 | Leabman |
| 2020/0192427 | A1 | 6/2020 | Leabman |
| 2020/0192428 | A1 | 6/2020 | Leabman |
| 2020/0193326 | A1 | 6/2020 | Leabman |
| 2020/0195197 | A1 | 6/2020 | Leabman |
| 2020/0195293 | A1 | 6/2020 | Leabman |

FOREIGN PATENT DOCUMENTS

| | | |
|---|---|---|
| WO | 2017163245 | 9/2017 |
| WO | 2019071138 | 4/2019 |
| WO | 2019198567 | 10/2019 |
| WO | 2019217461 | 11/2019 |
| WO | 2020006077 | 1/2020 |
| WO | 2020037171 | 2/2020 |

OTHER PUBLICATIONS

"Contributes to longer healthy life expectancy with non-invasive vital acquisition sensor," Quantum Operation Co., Ltd., presentation found on Jan. 12, 2021 at https://oi.nttdata.com/program/forum/history/20191118/pdf/03_quantum-op.pdf (14 pages including English translation).

International Search Report and Written Opinion for PCT/US2019/031176, dated Aug. 23, 2019, 9 pages.

Qiang et al., "Quantitative detection of glucose level based on radiofrequency patch biosensor combined with volume-fixed structures," Biosensors and Bioelectronics 98:357-363, 2017.

U.S. Appl. No. 17/123,947, titled "Non-Invasive Detection of an Analyte Using Decoupled Transmit and Receive Antennas," filed Dec. 16, 2020 (46 pages).

U.S. Appl. No. 17/123,961, titled "Non-Invasive Analyte Sensor and System With Decoupled and Inefficient Transmit and Receive Antennas," filed Dec. 16, 2020 (48 pages).

U.S. Appl. No. 17/123,977, titled "Non-Invasive Detection of an Analyte Using Decoupled and Inefficient Transmit and Receive Antennas," filed Dec. 16, 2020 (47 pages).

U.S. Appl. No. 17/123,992, titled "Non-Invasive Analyte Sensor Device," filed Dec. 16, 2020 (47 pages).

International Search Report and Written Opinion issued for International Patent Application No. PCT/IB2020/062222, dated Mar. 25, 2021, 7 pages.

Shaker, G. et al., "Non-Invasive Monitoring of Glucose Level Changes Utilizing a mm-Wave Radar System," IJMHCI, vol. 10, Issue 3 (2018): pp. 10-29.

Lien, J. et al., "Soli: Ubiquitous Gesture Sensing with Millimeter Wave Radar," ACM Trans. Graph., vol. 35, No. 4, Article 142, 19 pages (Jul. 2016).

* cited by examiner

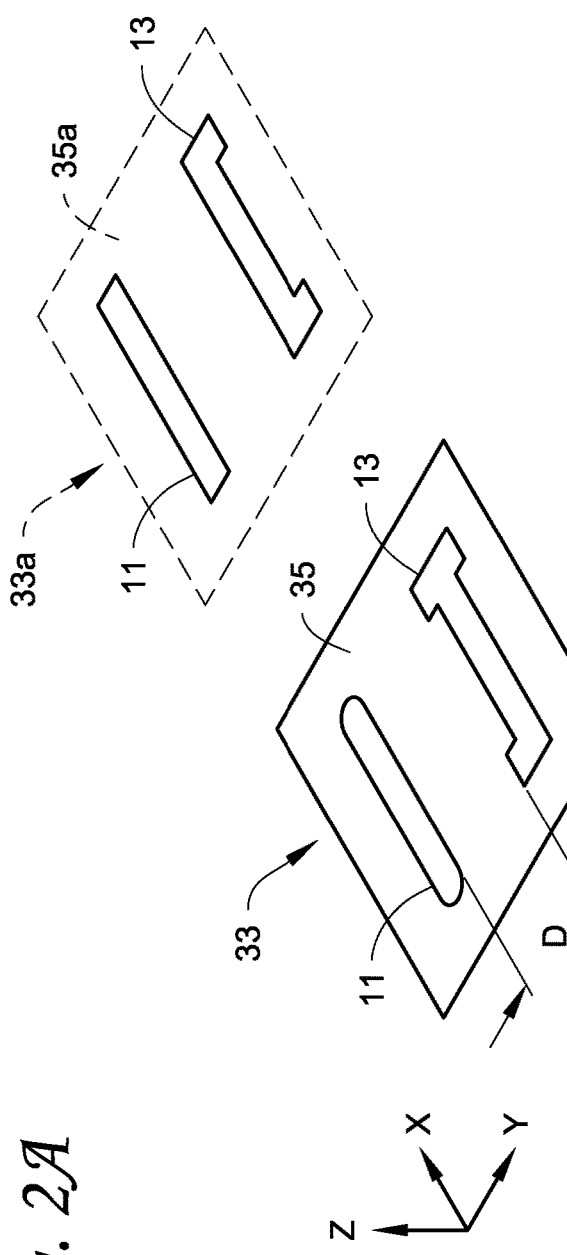
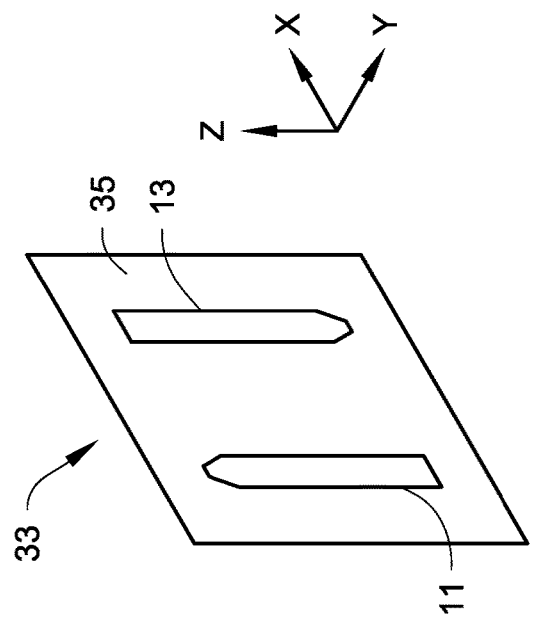
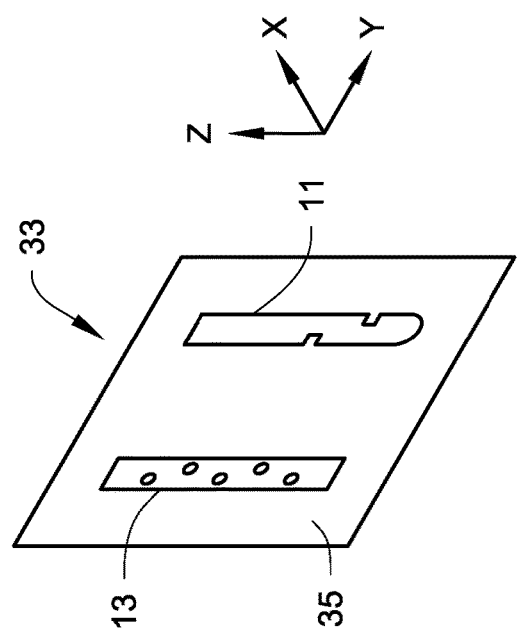
Fig. 2A
Fig. 2C
Fig. 2B

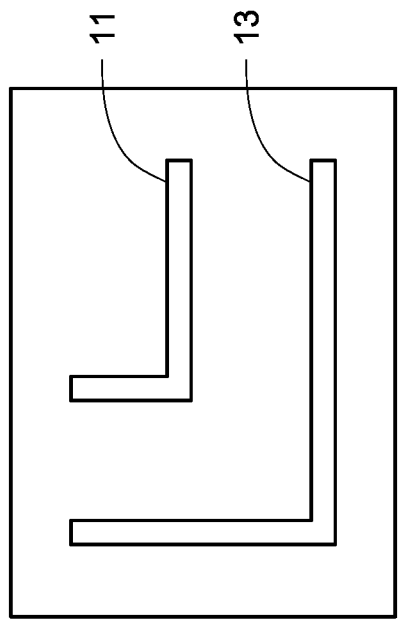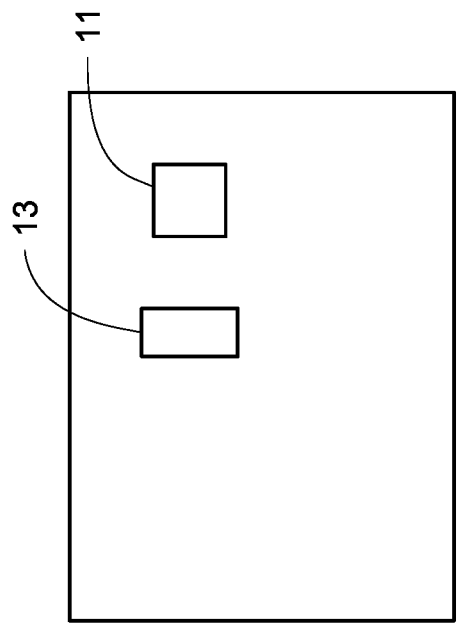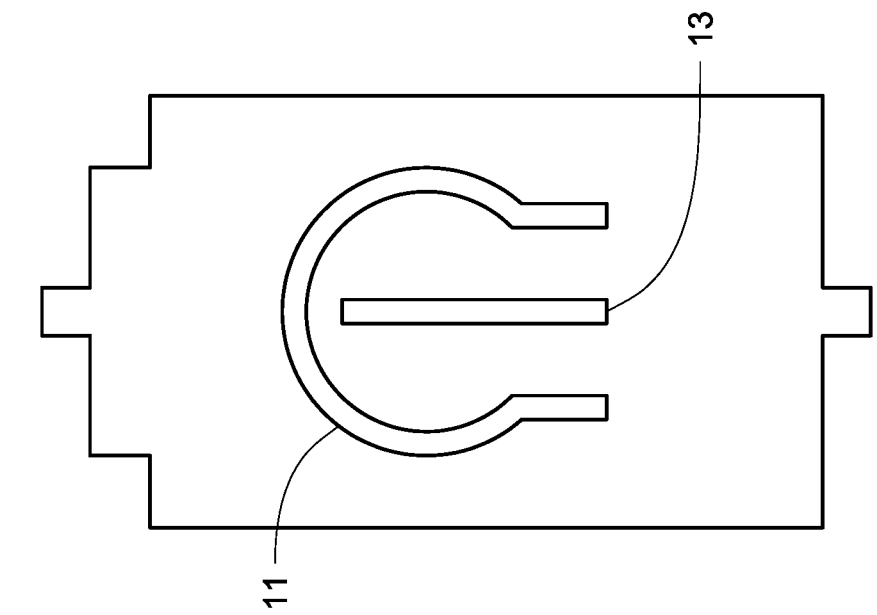

NON-INVASIVE ANALYTE SENSOR AND SYSTEM WITH DECOUPLED TRANSMIT AND RECEIVE ANTENNAS

FIELD

This disclosure relates generally to apparatus, systems and methods of non-invasively detecting an analyte via spectroscopic techniques using non-optical frequencies such as in the radio or microwave frequency bands of the electromagnetic spectrum. More specifically, this disclosure relates to a non-invasive analyte sensor that includes a transmit antenna and a receive antenna where the transmit and receive antennas are decoupled from one another.

BACKGROUND

There is interest in being able to detect and/or measure an analyte within a target. One example is measuring glucose in biological tissue. In the example of measuring glucose in a patient, current analyte measurement methods are invasive in that they perform the measurement on a bodily fluid such as blood for fingerstick or laboratory-based tests, or on fluid that is drawn from the patient often using an invasive transcutaneous device. There are non-invasive methods that claim to be able to perform glucose measurements in biological tissues. However many of the non-invasive methods generally suffer from: lack of specificity to the analyte of interest, such as glucose; interference from temperature fluctuations; interference from skin compounds (i.e. sweat) and pigments; and complexity of placement, i.e. the sensing device resides on multiple locations on the patient's body.

SUMMARY

This disclosure relates generally to apparatus, systems and methods of non-invasively detecting an analyte via spectroscopic techniques using non-optical frequencies such as in the radio or microwave frequency bands of the electromagnetic spectrum. A non-invasive analyte sensor described herein includes at least one transmit antenna (which may also be referred to as a transmit element) that functions to transmit a generated transmit signal in a radio or microwave frequency range of the electromagnetic spectrum into a target containing an analyte of interest, and at least one receive antenna (which may also be referred to as a receive element) that functions to detect a response resulting from transmission of the transmit signal by the transmit antenna into the target.

The transmit and receive antennas are decoupled from one another which helps to improve the detection capability of the non-invasive analyte sensor. The decoupling between the transmit and receive antennas can be achieved using any one or more techniques that causes as much of the signal as possible that is transmitted by the transmit antenna to enter the target and that minimizes or even eliminates the amount of electromagnetic energy that is directly received by the receive antenna from the transmit antenna without traveling into the target. The decoupling can be achieved by one or more intentionally fabricated configurations and/or arrangements between the transmit and receive antennas that is sufficient to decouple the transmit and receive antennas from one another. In one non-limiting embodiment, the decoupling can be achieved by the transmit antenna and the receive antenna having intentionally different geometries from one another. Intentionally different geometries refers to different geometric configurations of the transmit and receive antennas that are intentional, and is distinct from differences in geometry of transmit and receive antennas that may occur by accident or unintentionally, for example due to manufacturing errors or tolerances.

Another technique to achieve decoupling of the transmit and receive antennas is to use an appropriate spacing between each antenna, depending upon factors such as output power, size of the antennas, frequency, and the presence of any shielding, so as to force a proportion of the electromagnetic lines of force of the transmit signal into the target so they reach the analyte, thereby minimizing or eliminating as much as possible direct receipt of electromagnetic energy by the receive antenna directly from the transmit antenna without traveling into the target. This technique helps to ensure that the response detected by the receive antenna is measuring the analyte and is not just the transmitted signal flowing directly from the transmit antenna to the receive antenna. In one embodiment, the sensor can use a first pair of transmit and receive antennas that have a first spacing therebetween, and a second pair of transmit and receive antennas that have a second spacing therebetween that differs from the first spacing.

The techniques described herein can be used to detect the presence of the analyte of interest, as well an amount of the analyte or a concentration of the analyte within the target. The techniques described herein can be used to detect a single analyte or more than one analyte. The target can be any target, for example human or non-human, animal or non-animal, biological or non-biological, that contains the analyte(s) that one may wish to detect. For example, the target can include, but is not limited to, human tissue, animal tissue, plant tissue, an inanimate object, soil, a fluid, genetic material, or a microbe. The analyte(s) can be any analyte, for example human or non-human, animal or non-animal, biological or non-biological, that one may wish to detect. For example, the analyte(s) can include, but is not limited to, one or more of blood glucose, blood alcohol, white blood cells, or luteinizing hormone.

In one embodiment, a non-invasive analyte sensor system can include a decoupled antenna array having at least one transmit antenna and at least one receive antenna that are decoupled from one another. The at least one transmit antenna and the at least one receive antenna are positioned and arranged relative to a target containing at least one analyte of interest so that the at least one transmit antenna can transmit a transmit signal into the target, and so that the at least one receive antenna can detect a response. A transmit circuit is electrically connectable to the at least one transmit antenna. The transmit circuit is configured to generate a transmit signal to be transmitted by the at least one transmit antenna, where the transmit signal is in a radio or microwave frequency range of the electromagnetic spectrum. In addition, a receive circuit is electrically connectable to the at least one receive antenna. The receive circuit is configured to receive a response detected by the at least one receive antenna resulting from transmission of the transmit signal by the at least one transmit antenna into the target containing the at least one analyte of interest.

In one embodiment, the decoupling can be achieved by an intentional difference in geometry between the at least one transmit antenna and the at least one receive antenna. In another embodiment, decoupling can be achieved by arranging the at least one transmit antenna and the at least one receive antenna with an appropriate spacing therebetween that is sufficient to decouple the at least one transmit antenna and the at least one receive antenna.

In another embodiment described herein, a non-invasive analyte sensor system can include a sensor housing and a decoupled detector array attached to the sensor housing. The decoupled detector array can have at least one transmit element and at least one receive element. The at least one transmit element can have a first geometry and the at least one receive element can have a second geometry that is geometrically different from the first geometry. In addition to or separately from the different geometries, an appropriate spacing can be provided between the at least one transmit element and the at least one receive element that is sufficient to decouple the transmit and receive elements from one another. The at least one transmit element is positioned and arranged to transmit a transmit signal into a target containing at least one analyte of interest and the at least one receive element is positioned and arranged to be able to detect a response. In this embodiment, the at least one transmit element consists of a strip of conductive material having at least one lateral dimension thereof greater than a thickness dimension thereof, and the strip of conductive material of the at least one transmit element is disposed on a substrate. In addition, in this embodiment, the at least one receive element consists of a strip of conductive material having at least one lateral dimension thereof greater than a thickness dimension thereof, and the strip of conductive material of the at least one receive element is disposed on a substrate which can be the same substrate or a different substrate than the at least one transmit element. A transmit circuit is attached to the sensor housing and is electrically connectable to the at least one transmit element, where the transmit circuit is configured to generate a transmit signal to be transmitted by the at least one transmit element, with the transmit signal being in a radio or microwave frequency range of the electromagnetic spectrum. In addition, a receive circuit is attached to the sensor housing, and is electrically connectable to the at least one receive element. The receive circuit is configured to receive a response detected by the at least one receive element resulting from transmission of the transmit signal by the at the least one transmit element into the target containing the at least one analyte of interest.

In still another embodiment described herein, a non-invasive analyte sensor system can include a sensor housing and a detector array attached to the sensor housing. The detector array can have at least one transmit element and at least one receive element that are decoupled from one another. The at least one transmit element can have a first geometry and the at least one receive element can have a second geometry that is geometrically different from the first geometry. In addition to or separately from the different geometries, an appropriate spacing can be provided between the at least one transmit element and the at least one receive element that is sufficient to decouple the transmit and receive elements from one another. The at least one transmit element is positioned and arranged to transmit a transmit signal into a target containing at least one analyte of interest and the at least one receive element is positioned and arranged to be able to detect a response. In this embodiment, the at least one transmit element and the at least one receive element can both consist of a strip of conductive material disposed on a substrate. A transmit circuit is disposed within the sensor housing and is electrically connected to the at least one transmit element. The transmit circuit is configured to generate a transmit signal to be transmitted by the at least one transmit element, where the transmit signal has at least two frequencies, each of which is in a range of about 10 kHz to about 100 GHz, for example about 300 MHz to about 6000 MHz. A receive circuit is also disposed within the sensor housing and is electrically connected to the at least one receive element. The receive circuit is configured to receive a response detected by the at least one receive element resulting from transmission of the transmit signal by the at least one transmit element into the target containing the at least one analyte of interest. In addition, a rechargeable battery is disposed within the sensor housing for providing electrical power to the detector array, the transmit circuit and the receive circuit.

DRAWINGS

References are made to the accompanying drawings that form a part of this disclosure, and which illustrate embodiments in which the apparatus, systems and methods described in this specification can be practiced.

FIG. 1 is a schematic depiction of a non-invasive analyte sensor system with a non-invasive analyte sensor relative to a target according to an embodiment.

FIGS. 2A-C illustrate different example orientations of antenna arrays that can be used in the sensor system described herein.

FIGS. 3A-3I illustrate different examples of transmit and receive antennas with different geometries.

Like reference numbers represent like parts throughout.

DETAILED DESCRIPTION

Figure 1:
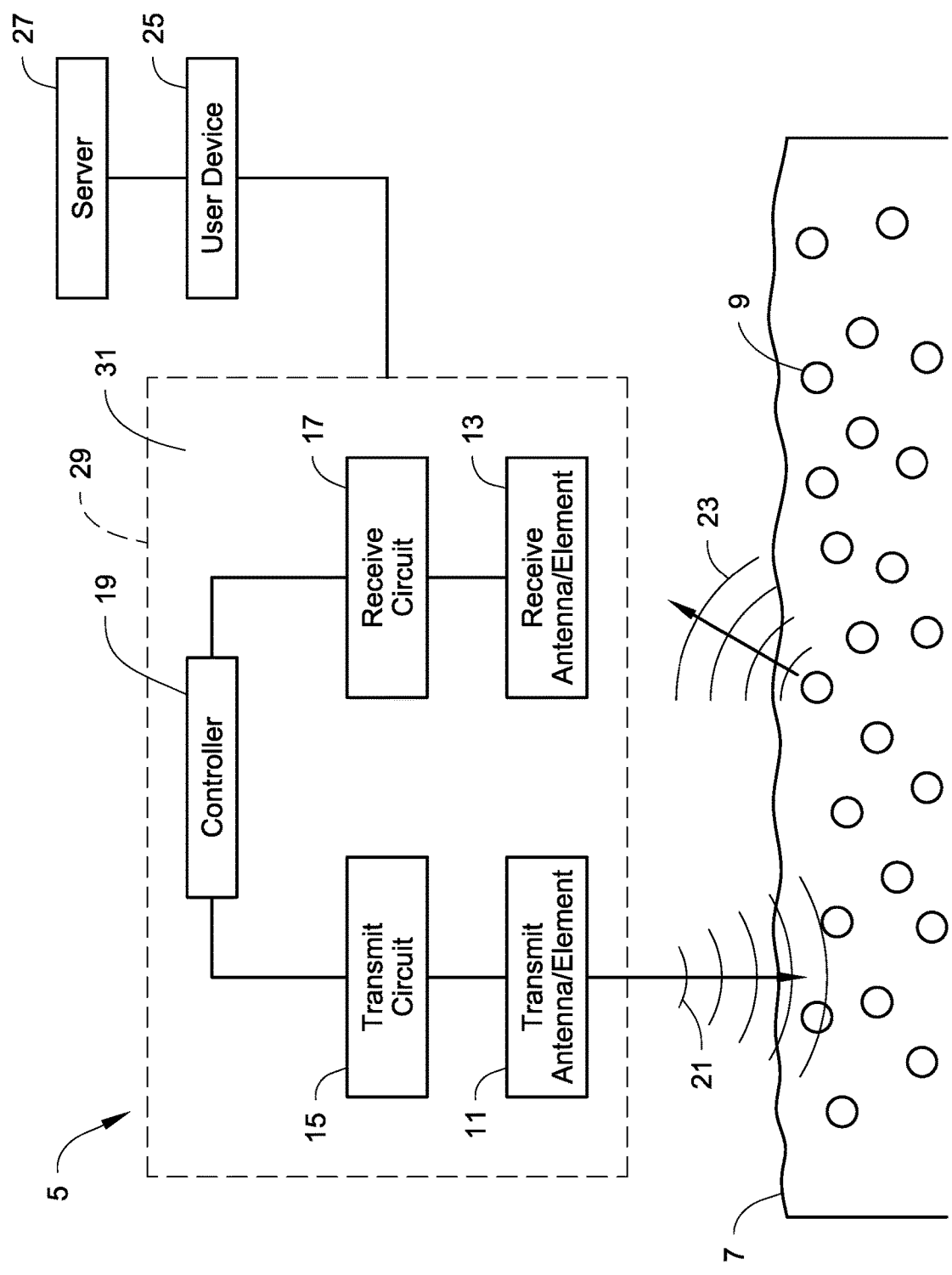

The following is a detailed description of apparatus, systems and methods of non-invasively detecting an analyte via spectroscopic techniques using non-optical frequencies such as in the radio or microwave frequency bands of the electromagnetic spectrum. A non-invasive analyte sensor includes a transmit antenna (which may also be referred to as a transmit element) that functions to transmit a generated transmit signal that is in a radio or microwave frequency range of the electromagnetic spectrum into a target containing an analyte of interest, and a receive antenna (which may also be referred to as a receive element) that functions to detect a response resulting from transmission of the transmit signal by the transmit antenna into the target. The transmit antenna and the receive antenna are decoupled from one another which improves the detection performance of the sensor.

The transmit antenna and the receive antenna can be located near the target and operated as further described herein to assist in detecting at least one analyte in the target. The transmit antenna transmits a signal, which has at least two frequencies in the radio or microwave frequency range, toward and into the target. The signal with the at least two frequencies can be formed by separate signal portions, each having a discrete frequency, that are transmitted separately at separate times at each frequency. In another embodiment, the signal with the at least two frequencies may be part of a complex signal that includes a plurality of frequencies including the at least two frequencies. The complex signal can be generated by blending or multiplexing multiple signals together followed by transmitting the complex signal whereby the plurality of frequencies are transmitted at the same time. One possible technique for generating the complex signal includes, but is not limited to, using an inverse Fourier transformation technique. The receive antenna detects a response resulting from transmission of the signal by the transmit antenna into the target containing the at least one analyte of interest.

The transmit antenna and the receive antenna are decoupled (which may also be referred to as detuned or the like) from one another. Decoupling refers to intentionally fabricating the configuration and/or arrangement of the transmit antenna and the receive antenna to minimize direct communication between the transmit antenna and the receive antenna, preferably absent shielding. Shielding between the transmit antenna and the receive antenna can be utilized. However, the transmit antenna and the receive antenna are decoupled even without the presence of shielding.

The signal(s) detected by the receive antenna can be analyzed to detect the analyte based on the intensity of the received signal(s) and reductions in intensity at one or more frequencies where the analyte absorbs the transmitted signal. An example of detecting an analyte using a non-invasive spectroscopy sensor operating in the radio or microwave frequency range of the electromagnetic spectrum is described in WO 2019/217461, the entire contents of which are incorporated herein by reference. The signal(s) detected by the receive antenna can be complex signals including a plurality of signal components, each signal component being at a different frequency. In an embodiment, the detected complex signals can be decomposed into the signal components at each of the different frequencies, for example through a Fourier transformation. In an embodiment, the complex signal detected by the receive antenna can be analyzed as a whole (i.e. without demultiplexing the complex signal) to detect the analyte as long as the detected signal provides enough information to make the analyte detection. In addition, the signal(s) detected by the receive antenna can be separate signal portions, each having a discrete frequency.

In one embodiment, the sensor described herein can be used to detect the presence of at least one analyte in a target. In another embodiment, the sensor described herein can detect an amount or a concentration of the at least one analyte in the target. The target can be any target containing at least one analyte of interest that one may wish to detect. The target can be human or non-human, animal or non-animal, biological or non-biological. For example, the target can include, but is not limited to, human tissue, animal tissue, plant tissue, an inanimate object, soil, a fluid, genetic material, or a microbe. Non-limiting examples of targets include, but are not limited to, a fluid, for example blood, interstitial fluid, cerebral spinal fluid, lymph fluid or urine, human tissue, animal tissue, plant tissue, an inanimate object, soil, genetic material, or a microbe.

The analyte(s) can be any analyte that one may wish to detect. The analyte can be human or non-human, animal or non-animal, biological or non-biological. For example, the analyte(s) can include, but is not limited to, one or more of blood glucose, blood alcohol, white blood cells, or luteinizing hormone. The analyte(s) can include, but is not limited to, a chemical, a combination of chemicals, a virus, a bacteria, or the like. The analyte can be a chemical included in another medium, with non-limiting examples of such media including a fluid containing the at least one analyte, for example blood, interstitial fluid, cerebral spinal fluid, lymph fluid or urine, human tissue, animal tissue, plant tissue, an inanimate object, soil, genetic material, or a microbe. The analyte(s) may also be a non-human, non-biological particle such as a mineral or a contaminant.

The analyte(s) can include, for example, naturally occurring substances, artificial substances, metabolites, and/or reaction products. As non-limiting examples, the at least one analyte can include, but is not limited to, insulin, acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; pro-BNP; BNP; troponin; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, polio virus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements;

transferrin; UDP-galactose-4-epimerase; urea; uroporphyrinogen I synthase; vitamin A; white blood cells; and zinc protoporphyrin.

The analyte(s) can also include one or more chemicals introduced into the target. The analyte(s) can include a marker such as a contrast agent, a radioisotope, or other chemical agent. The analyte(s) can include a fluorocarbon-based synthetic blood. The analyte(s) can include a drug or pharmaceutical composition, with non-limiting examples including ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The analyte(s) can include other drugs or pharmaceutical compositions. The analyte(s) can include neurochemicals or other chemicals generated within the body, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

Referring now to FIG. 1, an embodiment of a non-invasive analyte sensor system with a non-invasive analyte sensor 5 is illustrated. The sensor 5 is depicted relative to a target 7 that contains an analyte of interest 9. In this example, the sensor 5 is depicted as including an antenna array that includes a transmit antenna/element 11 (hereinafter "transmit antenna 11") and a receive antenna/element 13 (hereinafter "receive antenna 13"). The sensor 5 further includes a transmit circuit 15, a receive circuit 17, and a controller 19. As discussed further below, the sensor 5 can also include a power supply, such as a battery (not shown in FIG. 1).

The transmit antenna 11 is positioned, arranged and configured to transmit a signal 21 that is the radio frequency (RF) or microwave range of the electromagnetic spectrum into the target 7. The transmit antenna 11 can be an electrode or any other suitable transmitter of electromagnetic signals in the radio frequency (RF) or microwave range. The transmit antenna 11 can have any arrangement and orientation relative to the target 7 that is sufficient to allow the analyte sensing to take place. In one non-limiting embodiment, the transmit antenna 11 can be arranged to face in a direction that is substantially toward the target 7.

The signal 21 transmitted by the transmit antenna 11 is generated by the transmit circuit 15 which is electrically connectable to the transmit antenna 11. The transmit circuit 15 can have any configuration that is suitable to generate a transmit signal to be transmitted by the transmit antenna 11. Transmit circuits for generating transmit signals in the RF or microwave frequency range are well known in the art. In one embodiment, the transmit circuit 15 can include, for example, a connection to a power source, a frequency generator, and optionally filters, amplifiers or any other suitable elements for a circuit generating an RF or microwave frequency electromagnetic signal. In an embodiment, the signal generated by the transmit circuit 15 can have at least two discrete frequencies (i.e. a plurality of discrete frequencies), each of which is in the range from about 10 kHz to about 100 GHz. In another embodiment, each of the at least two discrete frequencies can be in a range from about 300 MHz to about 6000 MHz. In an embodiment, the transmit circuit 15 can be configured to sweep through a range of frequencies that are within the range of about 10 kHz to about 100 GHz, or in another embodiment a range of about 300 MHz to about 6000 MHz. In an embodiment, the transmit circuit 15 can be configured to produce a complex transmit signal, the complex signal including a plurality of signal components, each of the signal components having a different frequency. The complex signal can be generated by blending or multiplexing multiple signals together followed by transmitting the complex signal whereby the plurality of frequencies are transmitted at the same time.

The receive antenna 13 is positioned, arranged, and configured to detect one or more electromagnetic response signals 23 that result from the transmission of the transmit signal 21 by the transmit antenna 11 into the target 7 and impinging on the analyte 9. The receive antenna 13 can be an electrode or any other suitable receiver of electromagnetic signals in the radio frequency (RF) or microwave range. In an embodiment, the receive antenna 13 is configured to detect electromagnetic signals having at least two frequencies, each of which is in the range from about 10 kHz to about 100 GHz, or in another embodiment a range from about 300 MHz to about 6000 MHz. The receive antenna 13 can have any arrangement and orientation relative to the target 7 that is sufficient to allow detection of the response signal(s) 23 to allow the analyte sensing to take place. In one non-limiting embodiment, the receive antenna 13 can be arranged to face in a direction that is substantially toward the target 7.

The receive circuit 17 is electrically connectable to the receive antenna 13 and conveys the received response from the receive antenna 13 to the controller 19. The receive circuit 17 can have any configuration that is suitable for interfacing with the receive antenna 13 to convert the electromagnetic energy detected by the receive antenna 13 into one or more signals reflective of the response signal(s) 23. The construction of receive circuits are well known in the art. The receive circuit 17 can be configured to condition the signal(s) prior to providing the signal(s) to the controller 19, for example through amplifying the signal(s), filtering the signal(s), or the like. Accordingly, the receive circuit 17 may include filters, amplifiers, or any other suitable components for conditioning the signal(s) provided to the controller 19. In an embodiment, at least one of the receive circuit 17 or the controller 19 can be configured to decompose or demultiplex a complex signal, detected by the receive antenna 13, including a plurality of signal components each at different frequencies into each of the constituent signal components. In an embodiment, decomposing the complex signal can include applying a Fourier transform to the detected complex signal. However, decomposing or demultiplexing a received complex signal is optional. Instead, in an embodiment, the complex signal detected by the receive antenna can be analyzed as a whole (i.e. without demultiplexing the complex signal) to detect the analyte as long as the detected signal provides enough information to make the analyte detection.

The controller 19 controls the operation of the sensor 5. The controller 19, for example, can direct the transmit circuit 15 to generate a transmit signal to be transmitted by the transmit antenna 11. The controller 19 further receives signals from the receive circuit 17. The controller 19 can optionally process the signals from the receive circuit 17 to detect the analyte(s) 9 in the target 7. In one embodiment, the controller 19 may optionally be in communication with at least one external device 25 such as a user device and/or a remote server 27, for example through one or more wireless connections such as Bluetooth, wireless data connections such a 4G, 5G, LTE or the like, or Wi-Fi. If provided, the external device 25 and/or remote server 27 may process (or further process) the signals that the controller 19 receives from the receive circuit 17, for example to detect the analyte(s) 9. If provided, the external device 25 may be used to provide communication between the sensor 5 and the remote server 27, for example using a wired data connection or via a wireless data connection or Wi-Fi of the external device 25 to provide the connection to the remote server 27.

With continued reference to FIG. 1, the sensor 5 may include a sensor housing 29 (shown in dashed lines) that defines an interior space 31. Components of the sensor 5 may be attached to and/or disposed within the housing 29. For example, the transmit antenna 11 and the receive antenna 13 are attached to the housing 29. In some embodiments, the antennas 11, 13 may be entirely or partially within the interior space 31 of the housing 29. In some embodiments, the antennas 11, 13 may be attached to the housing 29 but at least partially or fully located outside the interior space 31. In some embodiments, the transmit circuit 15, the receive circuit 17 and the controller 19 are attached to the housing 29 and disposed entirely within the sensor housing 29.

The receive antenna 13 is decoupled or detuned with respect to the transmit antenna 11 such that electromagnetic coupling between the transmit antenna 11 and the receive antenna 13 is reduced. The decoupling of the transmit antenna 11 and the receive antenna 13 increases the portion of the signal(s) detected by the receive antenna 13 that is the response signal(s) 23 from the target 7, and minimizes direct receipt of the transmitted signal 21 by the receive antenna 13. The decoupling of the transmit antenna 11 and the receive antenna 13 results in transmission from the transmit antenna 11 to the receive antenna 13 having a reduced forward gain ($S_{21}$) and an increased reflection at output ($S_{22}$) compared to antenna systems having coupled transmit and receive antennas.

In an embodiment, coupling between the transmit antenna 11 and the receive antenna 13 is 95% or less. In another embodiment, coupling between the transmit antenna 11 and the receive antenna 13 is 90% or less. In another embodiment, coupling between the transmit antenna 11 and the receive antenna 13 is 85% or less. In another embodiment, coupling between the transmit antenna 11 and the receive antenna 13 is 75% or less.

Any technique for reducing coupling between the transmit antenna 11 and the receive antenna 13 can be used. For example, the decoupling between the transmit antenna 11 and the receive antenna 13 can be achieved by one or more intentionally fabricated configurations and/or arrangements between the transmit antenna 11 and the receive antenna 13 that is sufficient to decouple the transmit antenna 11 and the receive antenna 13 from one another.

For example, in one embodiment described further below, the decoupling of the transmit antenna 11 and the receive antenna 13 can be achieved by intentionally configuring the transmit antenna 11 and the receive antenna 13 to have different geometries from one another. Intentionally different geometries refers to different geometric configurations of the transmit and receive antennas 11, 13 that are intentional. Intentional differences in geometry are distinct from differences in geometry of transmit and receive antennas that may occur by accident or unintentionally, for example due to manufacturing errors or tolerances.

Another technique to achieve decoupling of the transmit antenna 11 and the receive antenna 13 is to provide appropriate spacing between each antenna 11, 13 that is sufficient to decouple the antennas 11, 13 and force a proportion of the electromagnetic lines of force of the transmitted signal 21 into the target 7 thereby minimizing or eliminating as much as possible direct receipt of electromagnetic energy by the receive antenna 13 directly from the transmit antenna 11 without traveling into the target 7. The appropriate spacing between each antenna 11, 13 can be determined based upon factors that include, but are not limited to, the output power of the signal from the transmit antenna 11, the size of the antennas 11, 13, the frequency or frequencies of the transmitted signal, and the presence of any shielding between the antennas. This technique helps to ensure that the response detected by the receive antenna 13 is measuring the analyte 9 and is not just the transmitted signal 21 flowing directly from the transmit antenna 11 to the receive antenna 13. In some embodiments, the appropriate spacing between the antennas 11, 13 can be used together with the intentional difference in geometries of the antennas 11, 13 to achieve decoupling.

In one embodiment, the transmit signal that is transmitted by the transmit antenna 11 can have at least two different frequencies, for example upwards of 7 to 12 different and discrete frequencies. In another embodiment, the transmit signal can be a series of discrete, separate signals with each separate signal having a single frequency or multiple different frequencies.

In one embodiment, the transmit signal (or each of the transmit signals) can be transmitted over a transmit time that is less than, equal to, or greater than about 300 ms. In another embodiment, the transmit time can be than, equal to, or greater than about 200 ms. In still another embodiment, the transmit time can be less than, equal to, or greater than about 30 ms. The transmit time could also have a magnitude that is measured in seconds, for example 1 second, 5 seconds, 10 seconds, or more. In an embodiment, the same transmit signal can be transmitted multiple times, and then the transmit time can be averaged. In another embodiment, the transmit signal (or each of the transmit signals) can be transmitted with a duty cycle that is less than or equal to about 50%.

FIGS. 2A-2C illustrate examples of antenna arrays 33 that can be used in the sensor system 5 and how the antenna arrays 33 can be oriented. Many orientations of the antenna arrays 33 are possible, and any orientation can be used as long as the sensor 5 can perform its primary function of sensing the analyte 9.

In FIG. 2A, the antenna array 33 includes the transmit antenna 11 and the receive antenna 13 disposed on a substrate 35 which may be substantially planar. This example depicts the array 33 disposed substantially in an X-Y plane. In this example, dimensions of the antennas 11, 13 in the X and Y-axis directions can be considered lateral dimensions, while a dimension of the antennas 11, 13 in the Z-axis direction can be considered a thickness dimension. In this example, each of the antennas 11, 13 has at least one lateral dimension (measured in the X-axis direction and/or in the Y-axis direction) that is greater than the thickness dimension thereof (in the Z-axis direction). In other words, the transmit antenna 11 and the receive antenna 13 are each relatively flat or of relatively small thickness in the Z-axis direction compared to at least one other lateral dimension measured in the X-axis direction and/or in the Y-axis direction.

In use of the embodiment in FIG. 2A, the sensor and the array 33 may be positioned relative to the target 7 such that the target 7 is below the array 33 in the Z-axis direction or above the array 33 in the Z-axis direction whereby one of the faces of the antennas 11, 13 face toward the target 7. Alternatively, the target 7 can be positioned to the left or right sides of the array 33 in the X-axis direction whereby one of the ends of each one of the antennas 11, 13 face toward the target 7. Alternatively, the target 7 can be positioned to the sides of the array 33 in the Y-axis direction whereby one of the sides of each one of the antennas 11, 13 face toward the target 7.

The sensor 5 can also be provided with one or more additional antenna arrays in addition the antenna array 33. For example, FIG. 2A also depicts an optional second antenna array 33a that includes the transmit antenna 11 and the receive antenna 13 disposed on a substrate 35a which may be substantially planar. Like the array 33, the array 33a may also be disposed substantially in the X-Y plane, with the arrays 33, 33a spaced from one another in the X-axis direction.

In FIG. 2B, the antenna array 33 is depicted as being disposed substantially in the Y-Z plane. In this example, dimensions of the antennas 11, 13 in the Y and Z-axis directions can be considered lateral dimensions, while a dimension of the antennas 11, 13 in the X-axis direction can be considered a thickness dimension. In this example, each of the antennas 11, 13 has at least one lateral dimension (measured in the Y-axis direction and/or in the Z-axis direction) that is greater than the thickness dimension thereof (in the X-axis direction). In other words, the transmit antenna 11 and the receive antenna 13 are each relatively flat or of relatively small thickness in the X-axis direction compared to at least one other lateral dimension measured in the Y-axis direction and/or in the Z-axis direction.

In use of the embodiment in FIG. 2B, the sensor and the array 33 may be positioned relative to the target 7 such that the target 7 is below the array 33 in the Z-axis direction or above the array 33 in the Z-axis direction whereby one of the ends of each one of the antennas 11, 13 face toward the target 7. Alternatively, the target 7 can be positioned in front of or behind the array 33 in the X-axis direction whereby one of the faces of each one of the antennas 11, 13 face toward the target 7. Alternatively, the target 7 can be positioned to one of the sides of the array 33 in the Y-axis direction whereby one of the sides of each one of the antennas 11, 13 face toward the target 7.

In FIG. 2C, the antenna array 33 is depicted as being disposed substantially in the X-Z plane. In this example, dimensions of the antennas 11, 13 in the X and Z-axis directions can be considered lateral dimensions, while a dimension of the antennas 11, 13 in the Y-axis direction can be considered a thickness dimension. In this example, each of the antennas 11, 13 has at least one lateral dimension (measured in the X-axis direction and/or in the Z-axis direction) that is greater than the thickness dimension thereof (in the Y-axis direction). In other words, the transmit antenna 11 and the receive antenna 13 are each relatively flat or of relatively small thickness in the Y-axis direction compared to at least one other lateral dimension measured in the X-axis direction and/or in the Z-axis direction.

In use of the embodiment in FIG. 2C, the sensor and the array 33 may be positioned relative to the target 7 such that the target 7 is below the array 33 in the Z-axis direction or above the array 33 in the Z-axis direction whereby one of the ends of each one of the antennas 11, 13 face toward the target 7. Alternatively, the target 7 can be positioned to the left or right sides of the array 33 in the X-axis direction whereby one of the sides of each one of the antennas 11, 13 face toward the target 7. Alternatively, the target 7 can be positioned in front of or in back of the array 33 in the Y-axis direction whereby one of the faces of each one of the antennas 11, 13 face toward the target 7.

The arrays 33, 33a in FIGS. 2A-2C need not be oriented entirely within a plane such as the X-Y plane, the Y-Z plane or the X-Z plane. Instead, the arrays 33, 33a can be disposed at angles to the X-Y plane, the Y-Z plane and the X-Z plane.

Decoupling Antennas Using Differences in Antenna Geometries

As mentioned above, one technique for decoupling the transmit antenna 11 from the receive antenna 13 is to intentionally configure the transmit antenna 11 and the receive antenna 13 to have intentionally different geometries. Intentionally different geometries refers to differences in geometric configurations of the transmit and receive antennas 11, 13 that are intentional, and is distinct from differences in geometry of the transmit and receive antennas 11, 13 that may occur by accident or unintentionally, for example due to manufacturing errors or tolerances when fabricating the antennas 11, 13.

The different geometries of the antennas 11, 13 may manifest itself, and may be described, in a number of different ways. For example, in a plan view of each of the antennas 11, 13 (such as in FIGS. 3A-I), the shapes of the perimeter edges of the antennas 11, 13 may be different from one another. The different geometries may result in the antennas 11, 13 having different surface areas in plan view. The different geometries may result in the antennas 11, 13 having different aspect ratios in plan view (i.e. a ratio of their sizes in different dimensions; for example, as discussed in further detail below, the ratio of the length divided by the width of the antenna 11 may be different than the ratio of the length divided by the width for the antenna 13). In some embodiments, the different geometries may result in the antennas 11, 13 having any combination of different perimeter edge shapes in plan view, different surface areas in plan view, and/or different aspect ratios. In some embodiments, the antennas 11, 13 may have one or more holes formed therein (see FIG. 2B) within the perimeter edge boundary, or one or more notches formed in the perimeter edge (see FIG. 2B).

So as used herein, a difference in geometry or a difference in geometrical shape of the antennas 11, 13 refers to any intentional difference in the figure, length, width, size, shape, area closed by a boundary (i.e. the perimeter edge), etc. when the respective antenna 11, 13 is viewed in a plan view.

The antennas 11, 13 can have any configuration and can be formed from any suitable material that allows them to perform the functions of the antennas 11, 13 as described herein. In one embodiment, the antennas 11, 13 can be formed by strips of material. A strip of material can include a configuration where the strip has at least one lateral dimension thereof greater than a thickness dimension thereof when the antenna is viewed in a plan view (in other words, the strip is relatively flat or of relatively small thickness compared to at least one other lateral dimension, such as length or width when the antenna is viewed in a plan view as in FIGS. 3A-I). A strip of material can include a wire. The antennas 11, 13 can be formed from any suitable conductive material(s) including metals and conductive non-metallic materials. Examples of metals that can be used include, but are not limited to, copper or gold. Another example of a material that can be used is non-metallic materials that are doped with metallic material to make the non-metallic material conductive.

In FIGS. 2A-2C, the antennas 11, 13 within each one of the arrays 33, 33a have different geometries from one another. In addition, FIGS. 3A-I illustrate plan views of additional examples of the antennas 11, 13 having different geometries from one another. The examples in FIGS. 2A-2C and 3A-I are not exhaustive and many different configurations are possible.

Figure 3A:
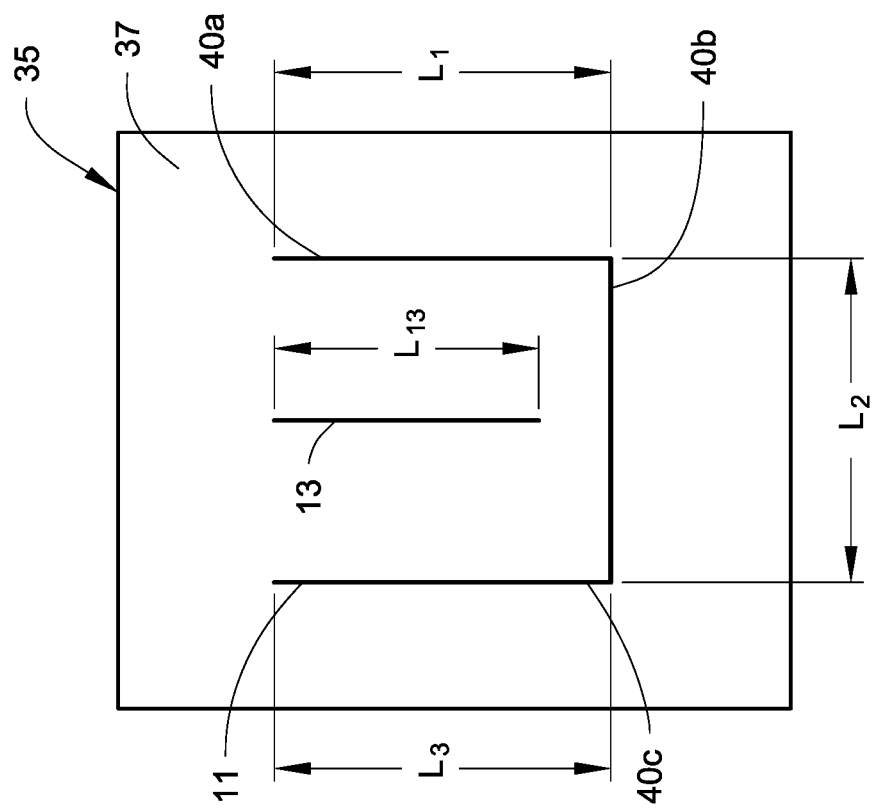

With reference initially to FIG. 3A, a plan view of an antenna array having two antennas with different geometries is illustrated. In this example (as well as for the examples in FIGS. 2A-2C and 3B-3I), for sake of convenience in describing the concepts herein, one antenna is labeled as the transmit antenna 11 and the other antenna is labeled as the receive antenna 13. However, the antenna labeled as the transmit antenna 11 could be the receive antenna 13, while the antenna labeled as the receive antenna 13 could be the transmit antenna 11. Each of the antennas 11, 13 are disposed on the substrate 35 having a planar surface 37.

The antennas 11, 13 can be formed as linear strips or traces on the surface 37. In this example, the antenna 11 is generally U-shaped and has a first linear leg 40a, a second linear leg 40b that extends perpendicular to the first leg 40a, and a third linear leg 40c that extends parallel to the leg 40a. Likewise, the antenna 13 is formed by a single leg that extends parallel to, and between, the legs 40a, 40c.

In the example depicted in FIG. 3A, each one of the antennas 11, 13 has at least one lateral dimension that is greater than a thickness dimension thereof (in FIG. 3A, the thickness dimension would extend into/from the page when viewing FIG. 3A). For example, the leg 40a of the antenna 11 extends in one direction (i.e. a lateral dimension) an extent that is greater than a thickness dimension of the leg 40a extending into or out of the page; the leg 40b of the antenna 11 extends in a direction (i.e. a lateral dimension) an extent that is greater than a thickness dimension of the leg 40b extending into or out of the page; and the leg 40c of the antenna 11 extends in one direction (i.e. a lateral dimension) an extent that is greater than a thickness dimension of the leg 40c extending into or out of the page. Likewise, the antenna 13 extends in one direction (i.e. a lateral dimension) an extent that is greater than a thickness dimension of the antenna 13 extending into or out of the page.

The antennas 11, 13 also differ in geometry from one another in that the total linear length of the antenna 11 (determined by adding the individual lengths $L_1$, $L_2$, $L_3$ of the legs 40a-c together) when viewed in plan view is greater than the length $L_{13}$ of the antenna 13 when viewed in plan view.

Figure 3B:
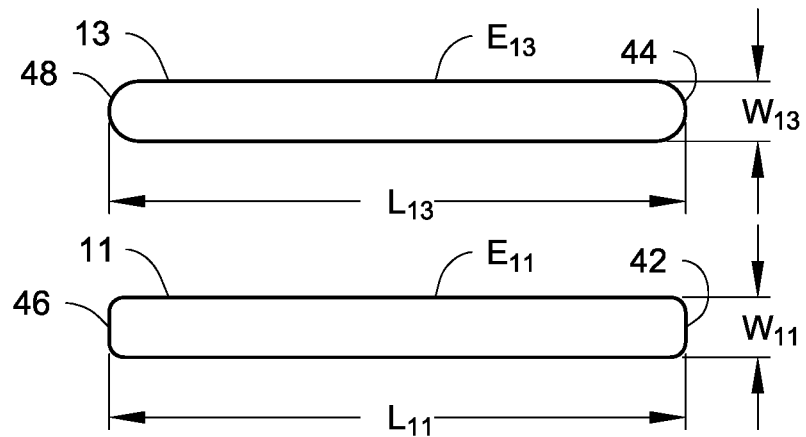

FIG. 3B illustrates another plan view of an antenna array having two antennas with different geometries. In this example, the antennas 11, 13 are illustrated as substantially linear strips each with a lateral length $L_{11}$, $L_{13}$, a lateral width $W_{11}$, $W_{13}$, and a perimeter edge $E_{11}$, $E_{13}$. The perimeter edges $E_{11}$, $E_{13}$ extend around the entire periphery of the antennas 11, 13 and bound an area in plan view. In this example, the lateral length $L_{11}$, $L_{13}$ and/or the lateral width $W_{11}$, $W_{13}$ is greater than a thickness dimension of the antennas 11, 13 extending into/from the page when viewing FIG. 3B. In this example, the antennas 11, 13 differ in geometry from one another in that the shapes of the ends of the antennas 11, 13 differ from one another. For example, when viewing FIG. 3B, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. It is also possible that the lateral lengths $L_{11}$, $L_{13}$ and/or the lateral widths $W_{11}$, $W_{13}$ of the antennas 11, 13 could differ from one another.

Figure 3C:
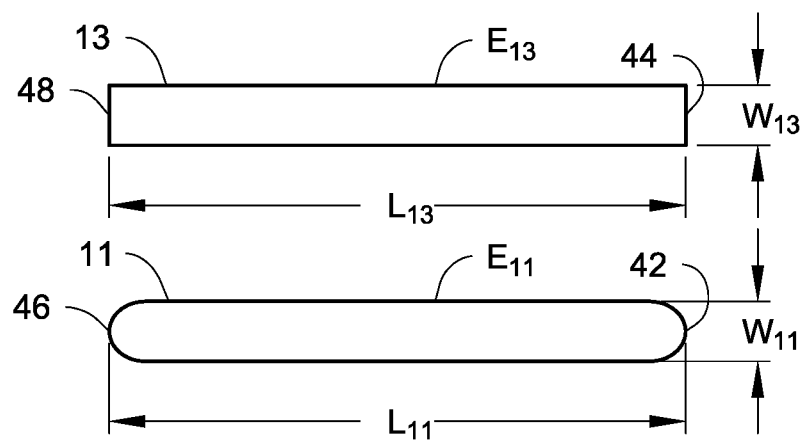

FIG. 3C illustrates another plan view of an antenna array having two antennas with different geometries that is somewhat similar to FIG. 3B. In this example, the antennas 11, 13 are illustrated as substantially linear strips each with the lateral length $L_{11}$, $L_{13}$, the lateral width $W_{11}$, $W_{13}$, and the perimeter edge $E_{11}$, $E_{13}$. The perimeter edges $E_{11}$, $E_{13}$ extend around the entire periphery of the antennas 11, 13 and bound an area in plan view. In this example, the lateral length $L_{11}$, $L_{13}$ and/or the lateral width $W_{11}$, $W_{13}$ is greater than a thickness dimension of the antennas 11, 13 extending into/from the page when viewing FIG. 3C. In this example, the antennas 11, 13 differ in geometry from one another in that the shapes of the ends of the antennas 11, 13 differ from one another. For example, when viewing FIG. 3C, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. In addition, the lateral widths $W_{11}$, $W_{13}$ of the antennas 11, 13 differ from one another. It is also possible that the lateral lengths $L_{11}$, $L_{13}$ of the antennas 11, 13 could differ from one another.

Figure 3D:
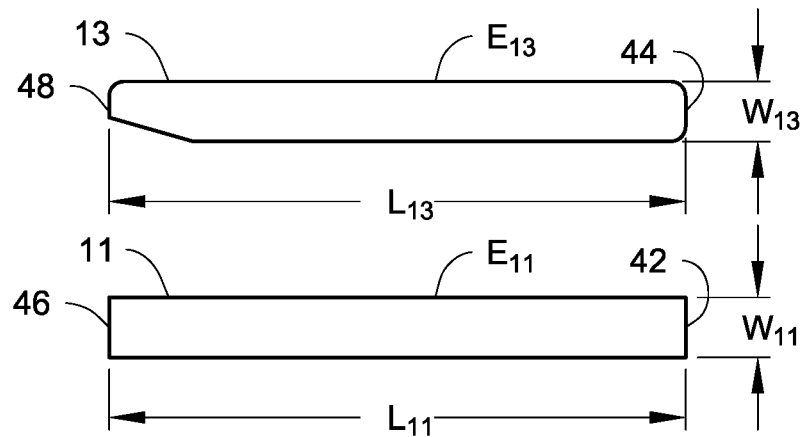

FIG. 3D illustrates another plan view of an antenna array having two antennas with different geometries that is somewhat similar to FIGS. 3B and 3C. In this example, the antennas 11, 13 are illustrated as substantially linear strips each with the lateral length $L_{11}$, $L_{13}$, the lateral width $W_{11}$, $W_{13}$, and the perimeter edge $E_{11}$, $E_{13}$. The perimeter edges $E_{11}$, $E_{13}$ extend around the entire periphery of the antennas 11, 13 and bound an area in plan view. In this example, the lateral length $L_{11}$, $L_{13}$ and/or the lateral width $W_{11}$, $W_{13}$ is greater than a thickness dimension of the antennas 11, 13 extending into/from the page when viewing FIG. 3D. In this example, the antennas 11, 13 differ in geometry from one another in that the shapes of the ends of the antennas 11, 13 differ from one another. For example, when viewing FIG. 3D, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. In addition, the lateral widths $W_{11}$, $W_{13}$ of the antennas 11, 13 differ from one another. It is also possible that the lateral lengths $L_{11}$, $L_{13}$ of the antennas 11, 13 could differ from one another.

FIG. 3E illustrates another plan view of an antenna array having two antennas with different geometries on a substrate. In this example, the antenna 11 is illustrated as being a strip of material having a generally horseshoe shape, while the antenna 13 is illustrated as being a strip of material that is generally linear. The planar shapes (i.e. geometries) of the antennas 11, 13 differ from one another. In addition, the total length of the antenna 11 (measured from one end to the other) when viewed in plan view is greater than the length of the antenna 13 when viewed in plan.

FIG. 3F illustrates another plan view of an antenna array having two antennas with different geometries on a substrate. In this example, the antenna 11 is illustrated as being a strip of material forming a right angle, and the antenna 13 is also illustrated as being a strip of material that forms a larger right angle. The planar shapes (i.e. geometries) of the antennas 11, 13 differ from one another since the total area in plan view of the antenna 13 is greater than the total area in plan view of the antenna 11. In addition, the total length of the antenna 11 (measured from one end to the other) when viewed in plan view is less than the length of the antenna 13 when viewed in plan.

FIG. 3G illustrates another plan view of an antenna array having two antennas with different geometries on a substrate. In this example, the antenna 11 is illustrated as being a strip of material forming a square, and the antenna 13 is illustrated as being a strip of material that forms a rectangle. The planar shapes (i.e. geometries) of the antennas 11, 13 differ from one another. In addition, at least one of the width/length of the antenna 11 when viewed in plan view is less than one of the width/length of the antenna 13 when viewed in plan.

Figure 3I:
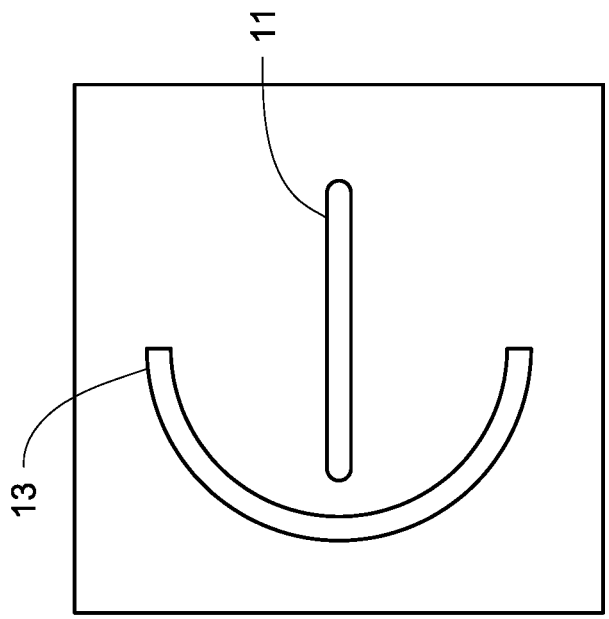
Figure 3H:
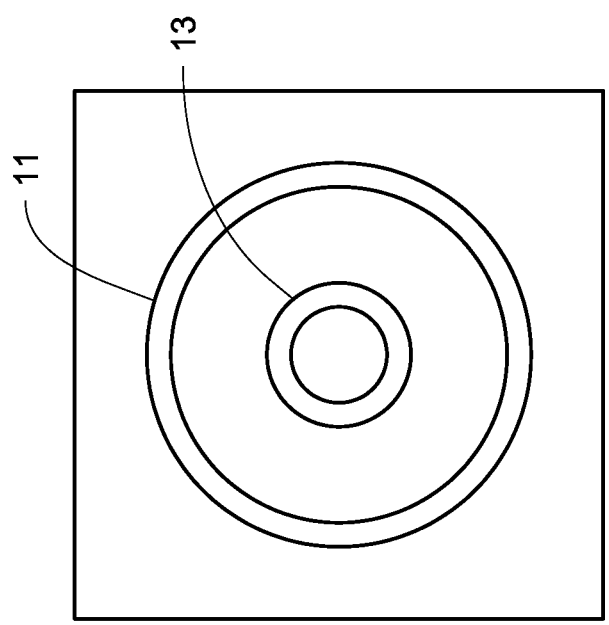

FIG. 3H illustrates another plan view of an antenna array having two antennas with different geometries on a substrate. In this example, the antenna 11 is illustrated as being a strip of material forming a circle when viewed in plan, and the antenna 13 is also illustrated as being a strip of material that forms a smaller circle when viewed in plan surrounded by the circle formed by the antenna 11. The planar shapes (i.e. geometries) of the antennas 11, 13 differ from one another due to the different sizes of the circles.

FIG. 3I illustrates another plan view of an antenna array having two antennas with different geometries on a substrate. In this example, the antenna 11 is illustrated as being a linear strip of material, and the antenna 13 is illustrated as being a strip of material that forms a semi-circle when viewed in plan. The planar shapes (i.e. geometries) of the antennas 11, 13 differ from one another due to the different shapes/geometries of the antennas 11, 13.

Figure 4A:
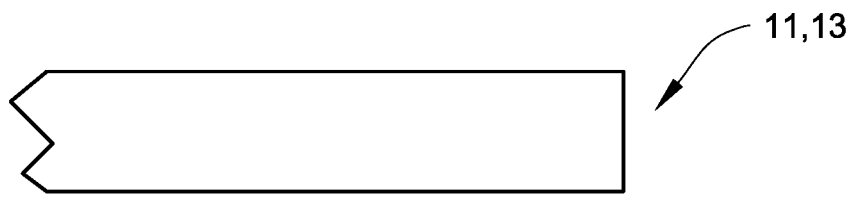
FIGS. 4A, 4B, 4C and 4D illustrate additional examples of different shapes that the ends of the transmit and receive antennas can have.
Figure 4B:
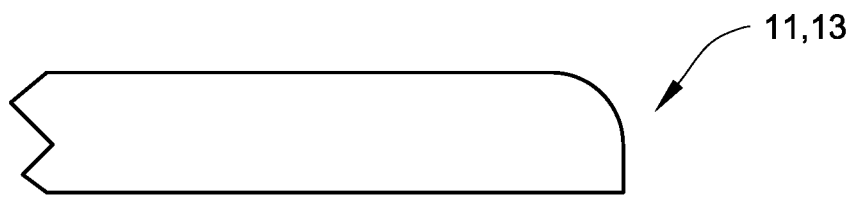
Figure 4C:
Figure 4D:
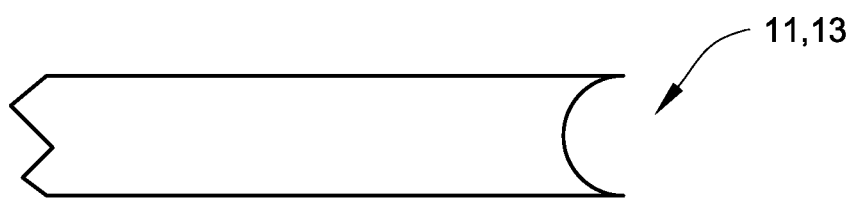

4A-D are plan views of additional examples of different shapes that the ends of the transmit and receive antennas 11, 13 can have to achieve differences in geometry. Either one of, or both of, the ends of the antennas 11, 13 can have the shapes in FIGS. 4A-D, including in the embodiments in FIGS. 3A-I. FIG. 4A depicts the end as being generally rectangular. FIG. 4B depicts the end as having one rounded corner while the other corner remains a right angle. FIG. 4C depicts the entire end as being rounded or outwardly convex. FIG. 4D depicts the end as being inwardly concave. Many other shapes are possible.

Another technique to achieve decoupling of the antennas 11, 13 is to use an appropriate spacing between each antenna 11, 13 with the spacing being sufficient to force most or all of the signal(s) transmitted by the transmit antenna 11 into the target, thereby minimizing the direct receipt of electromagnetic energy by the receive antenna 13 directly from the transmit antenna 11. The appropriate spacing can be used by itself to achieve decoupling of the antennas 11, 13. In another embodiment, the appropriate spacing can be used together with differences in geometry of the antennas 11, 13 to achieve decoupling.

Referring to FIG. 2A, there is a spacing D between the transmit antenna 11 and the receive antenna 13 at the location indicated. The spacing D between the antennas 11, 13 may be constant over the entire length (for example in the X-axis direction) of each antenna 11, 13, or the spacing D between the antennas 11, 13 could vary. Any spacing D can be used as long as the spacing D is sufficient to result in most or all of the signal(s) transmitted by the transmit antenna 11 reaching the target and minimizing the direct receipt of electromagnetic energy by the receive antenna 13 directly from the transmit antenna 11, thereby decoupling the antennas 11, 13 from one another.

Figure 5:
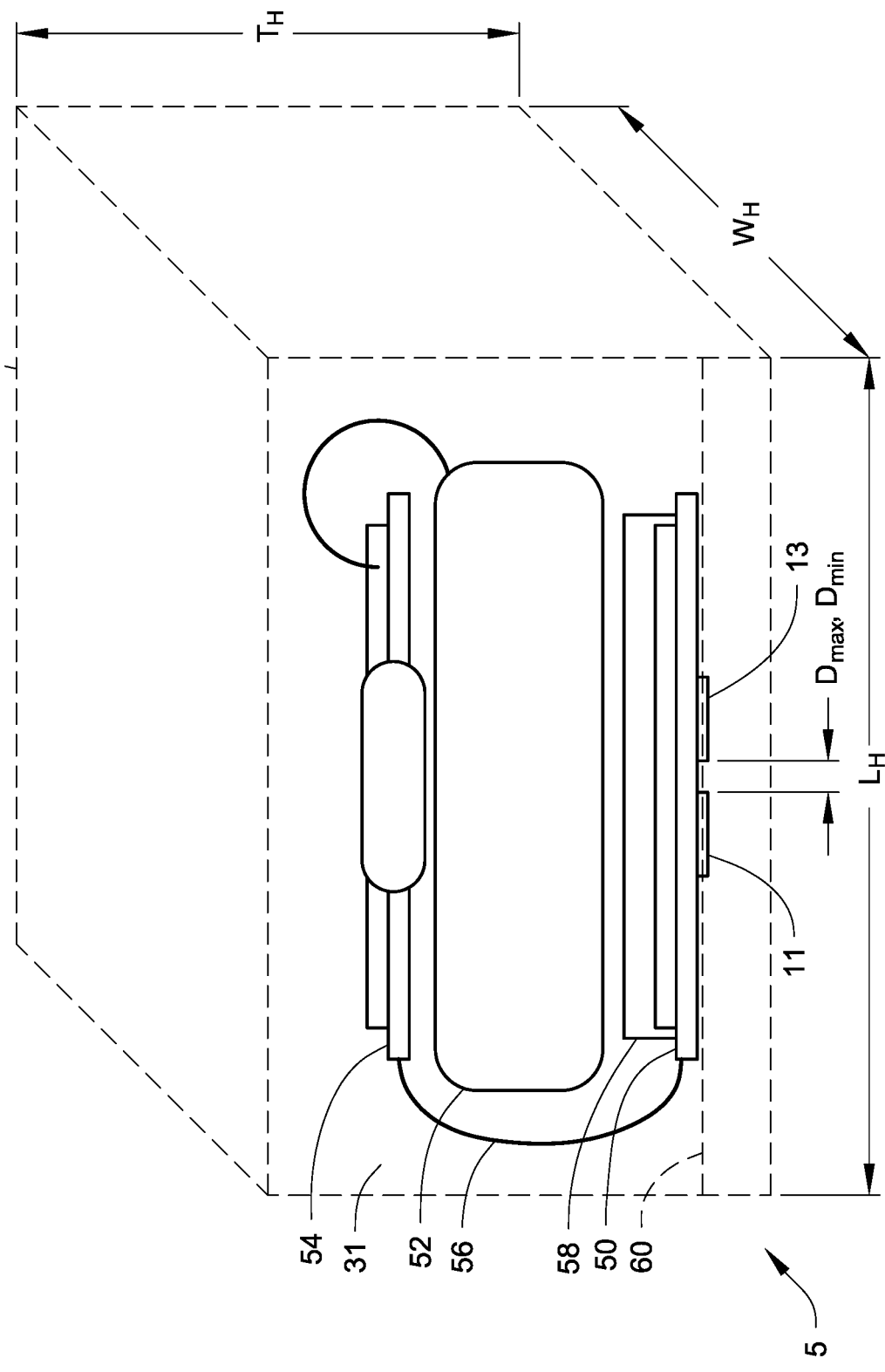
FIG. 5 is a schematic depiction of a sensor device according to an embodiment.

Referring to FIG. 5, an example configuration of the sensor device 5 is illustrated. In FIG. 5, elements that are identical or similar to elements in FIG. 1 are referenced using the same reference numerals. In FIG. 5, the antennas 11, 13 are disposed on one surface of a substrate 50 which can be, for example, a printed circuit board. At least one battery 52, such as a rechargeable battery, is provided above the substrate 50, for providing power to the sensor device 5. In addition, a digital printed circuit board 54 is provided on which the transmit circuit 15, the receive circuit 17, and the controller 19 and other electronics of the second device 5 can be disposed. The substrate 50 and the digital printed circuit board 54 are electrically connected via any suitable electrical connection, such as a flexible connector 56. An RF shield 58 may optionally be positioned between the antennas 11, 13 and the battery 52, or between the antennas 11, 13 and the digital printed circuit board 54, to shield the circuitry and electrical components from RF interference.

As depicted in FIG. 5, all of the elements of the sensor device 5, including the antennas 11, 13, the transmit circuit 15, the receive circuit 17, the controller 19, the battery 52 and the like are contained entirely within the interior space 31 of the housing 29. In an alternative embodiment, a portion of or the entirety of each antenna 11, 13 can project below a bottom wall 60 of the housing 29. In another embodiment, the bottom of each antenna 11, 13 can be level with the bottom wall 60, or they can be slightly recessed from the bottom wall 60.

The housing 29 of the sensor device 5 can have any configuration and size that one finds suitable for employing in a non-invasive sensor device. In one embodiment, the housing 29 can have a maximum length dimension $L_H$ no greater than 50 mm, a maximum width dimension $W_H$ no greater than 50 mm, and a maximum thickness dimension $T_H$ no greater than 25 mm, for a total interior volume of no greater than about 62.5 cm$^3$.

In addition, with continued reference to FIG. 5 together with FIGS. 3A-3I, there is preferably a maximum spacing $D_{max}$ and a minimum spacing $D_{min}$ between the transmit antenna 11 and the receive antenna 13. The maximum spacing $D_{max}$ may be dictated by the maximum size of the housing 29. In one embodiment, the maximum spacing $D_{max}$ can be about 50 mm. In one embodiment, the minimum spacing $D_{min}$ can be from about 1.0 mm to about 5.0 mm.

Figure 6:
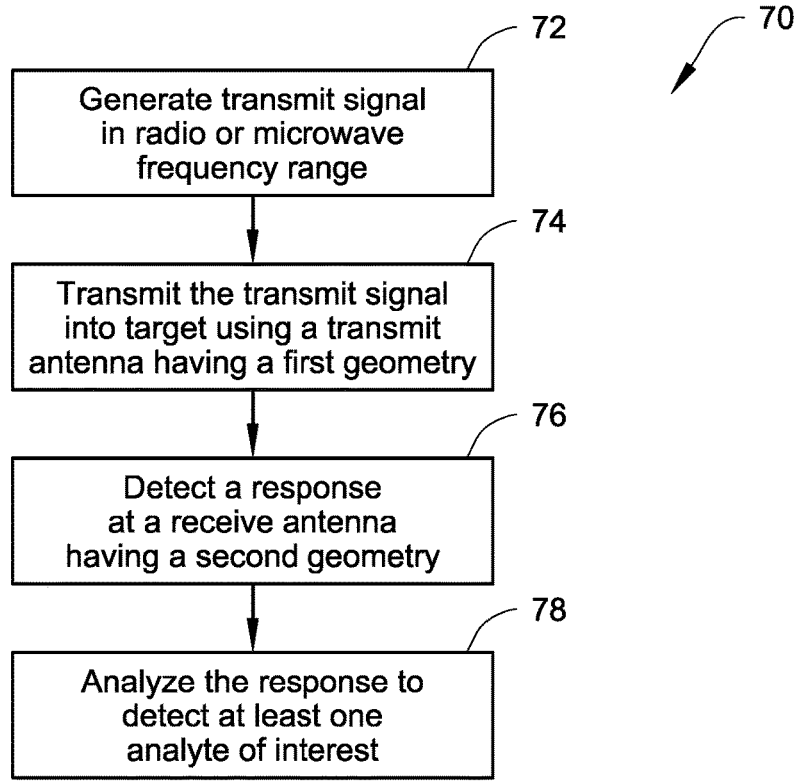
FIG. 6 is a flowchart of a method for detecting an analyte according to an embodiment.

With reference now to FIG. 6 together with FIG. 1, one embodiment of a method 70 for detecting at least one analyte in a target is depicted. The method in FIG. 6 can be practiced using any of the embodiments of the sensor device 5 described herein. In order to detect the analyte, the sensor device 5 is placed in relatively close proximity to the target. Relatively close proximity means that the sensor device 5 can be close to but not in direct physical contact with the target, or alternatively the sensor device 5 can be placed in direct, intimate physical contact with the target. The spacing between the sensor device 5 and the target 7 can be dependent upon a number of factors, such as the power of the transmitted signal. Assuming the sensor device 5 is properly positioned relative to the target 7, at box 72 the transmit signal is generated, for example by the transmit circuit 15. The transmit signal is then provided to the transmit antenna 11 which, at box 74, transmits the transmit signal toward and into the target. At box 76, a response resulting from the transmit signal contacting the analyte(s) is then detected by the receive antenna 13. The receive circuit 17 obtains the detected response from the receive antenna 13 and provides the detected response to the controller 19. At box 78, the detected response can then be analyzed to detect at least one analyte. The analysis can be performed by the controller 19 and/or by the external device 25 and/or by the remote server 27.

Figure 7:
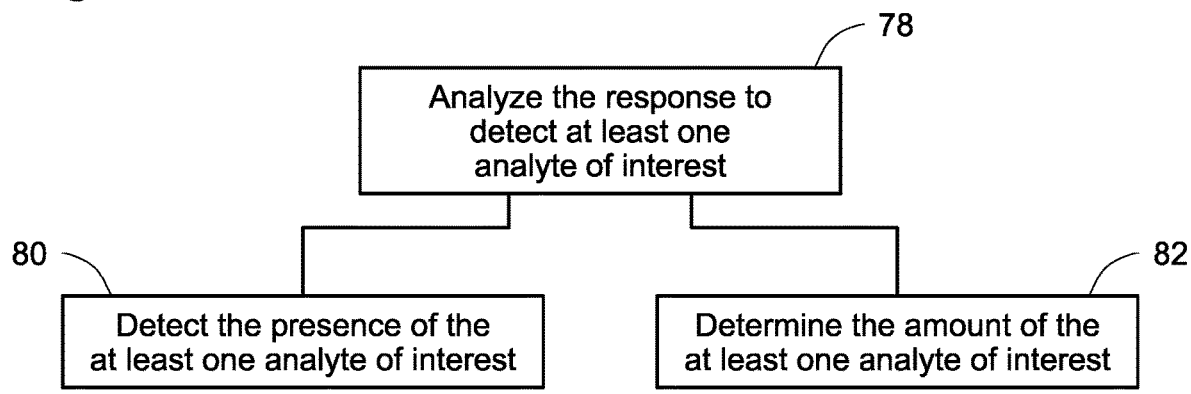
FIG. 7 is a flowchart of analysis of a response according to an embodiment.

Referring to FIG. 7, the analysis at box 78 in the method 70 can take a number of forms. In one embodiment, at box 80, the analysis can simply detect the presence of the analyte, i.e. is the analyte present in the target. Alternatively, at box 82, the analysis can determine the amount of the analyte that is present.

Figure 8:
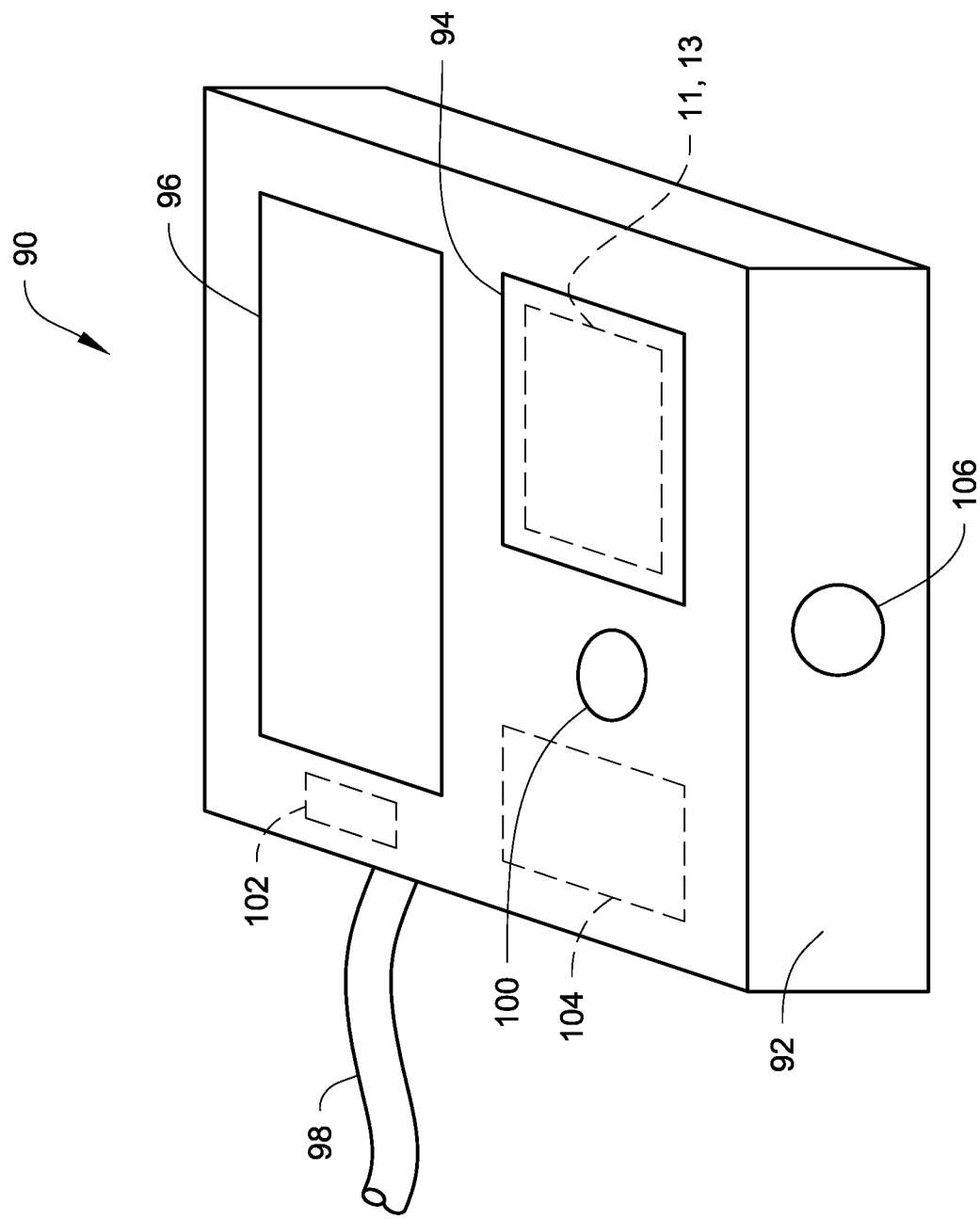
FIG. 8 illustrates a tabletop device that incorporates the non-invasive analyte sensor system described herein.

FIG. 8 illustrates another example application of the non-invasive analyte sensor 5. In this example, the sensor 5 is incorporated into a tabletop device 90. The term "tabletop" is used interchangeably with "countertop" and refers to a device that is intended to reside on a top surface of a structure such as, but not limited to, a table, counter, shelf, another device, or the like during use. In some embodiments, the device 90 can be mounted on a vertical wall. The device 90 is configured to obtain a real-time, on-demand reading of an analyte in a user such as, but not limited to, obtaining a glucose level reading of the user using the non-invasive analyte sensor 5 incorporated into the device 90.

The device 90 in FIG. 8 is illustrated as being generally rectangular box shaped. However, the device 90 can have other shapes such as cylindrical, square box, triangular and many other shapes. The device 90 includes a housing 92, a reading area 94, for example on a top surface of the housing 92, where the antennas 11, 13 of the sensor 5 are positioned to be able to obtain a reading, and a display screen 96, for example on the top surface of the housing 92, for displaying data such as results of a reading by the sensor 5. Power for the device 90 can be provided via a power cord 98 that plugs into a wall socket. The device 90 may also include one or more batteries which act as a primary power source for the device 90 instead of power provided via the power cord 98 or the one or more batteries can act as a back-up power source in the event power is not available via the power cord 98.

In operation of the device 90, a user places a body part adjacent to (i.e. in contact with or close to but not in contact with) the reading area 94. The body part can be any digit of the user's hand, such as the thumb, the index finger, the middle finger, the ring finger or the little finger; or the user's wrist; or any other body part of the user. A reading by the device 90 is triggered by the user. The device 90 can be configured in any manner with any form of a trigger mechanism to permit the user to trigger a reading. For example, the device 90 can be provided with a trigger button 100 located anywhere thereon that when pressed triggers a reading by the sensor 5. Alternatively, the device 90 can include a proximity sensor, for example associated with the reading area 94, that detects the presence of the user, such as the user's body part, adjacent to the reading area 94 and when detected initiates the reading. Alternatively, the device 90 can include a pressure sensor, for example associated with the reading area 94, that detects contact of the user's body part with the reading area 94 and when contact is detected triggers the reading by the sensor 5. Alternatively, the reading by the sensor 5 can be voice-triggered, for example by an optional microphone 102 of the device 90 that picks up a predetermined reading-initiating command that can be voiced by the user or a caregiver.

The results of a reading can be displayed on the display screen 96. For example, assuming the analyte being detected is glucose, the user's glucose reading can be displayed on the display screen 96. In addition (or alternatively), the results of the reading can be audibly presented by the device 90, for example via one or more speakers 104. The display screen 96 may be a touchscreen that permits user inputs, for example to scroll between different forms of display, or select different functionality of the device 90. Alternatively, one or more input buttons (not shown) can be provided on the device 90 to allow user inputs.

An on/off power button or switch 106 can be provided anywhere on the device 90 to power the device 90 on and off. The on/off power button or switch 106 could also function as the trigger button instead of the trigger button 100. Alternatively, the trigger button 100 may act as an on/off power button to power the device 90 on and off, as well as trigger a reading. In one embodiment, the device 90 can be provided with sleep functionality whereby the device 90 enters a low power sleep mode after a period of time of inactivity of the device 90. In the sleep mode, the trigger mechanism and/or the microphone 102 on the device 90 can remain active waiting for suitable action to bring the device 90 out of the sleep mode and ready to take a reading. Examples of suitable actions include, but are not limited to, actuation of the trigger mechanism or recognition of an audible voice command.

In some embodiments, the device 90 can include data storage for storing individual readings for later historical analysis. Data for different individual users can also be stored in separate files for each user.

Figure 10:
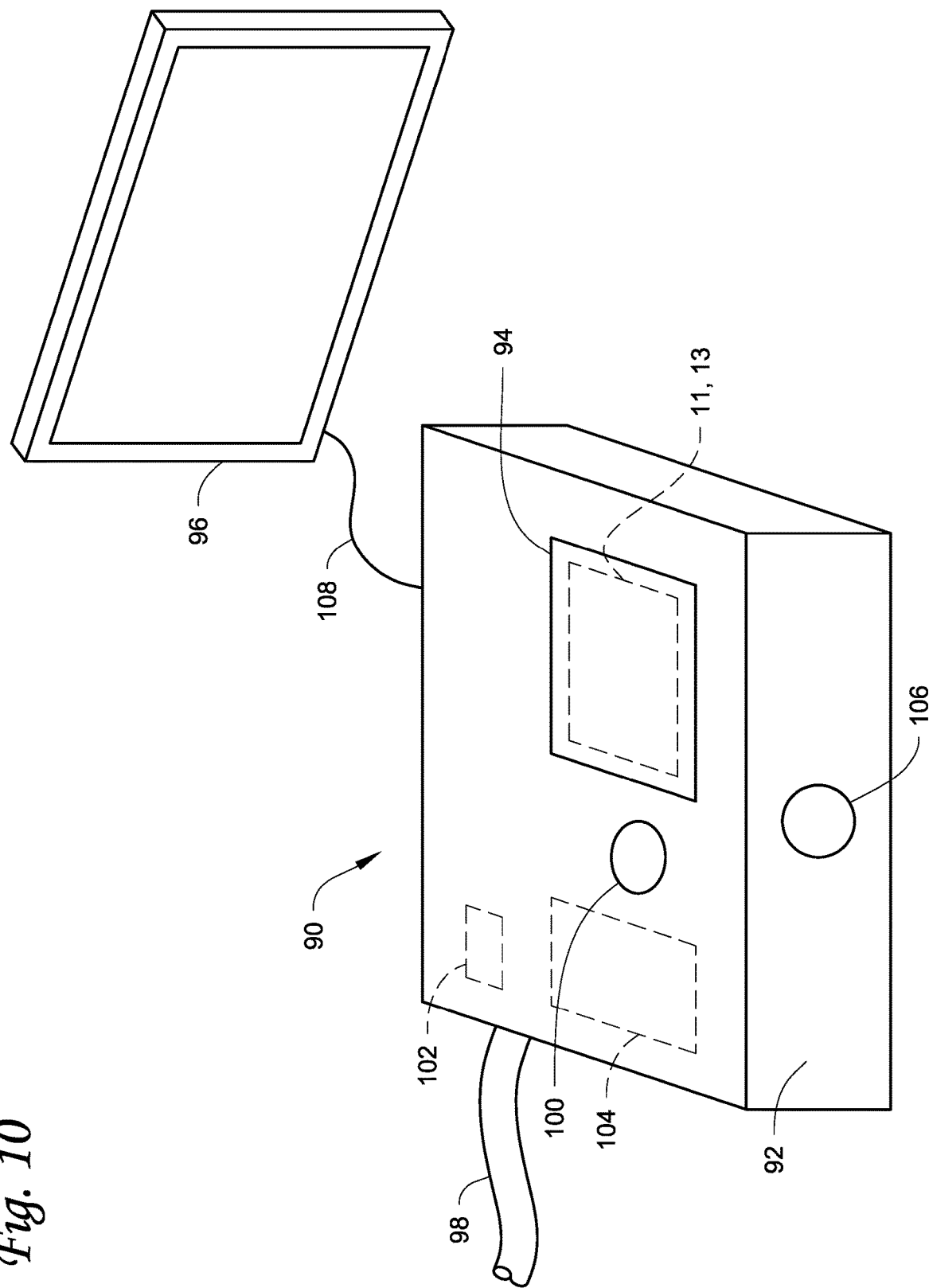
FIG. 10 illustrates another embodiment of a tabletop device that incorporates the non-invasive analyte sensor system described herein.

FIG. 10 illustrates another embodiment of the tabletop device 90 that is similar to the device 90 in FIG. 8 and features that are similar to features in FIG. 8 are referenced using the same reference numbers. In FIG. 10, instead of the display screen 96 being integrated into the device 90, the display screen 96 is part of a separate device that is suitably connected to the device 90 for example by a cable 108 such as a USB cable. The separate display screen 96 in FIG. 10 may receive power from the device 90, or the separate display screen 96 may have its own power source. In one embodiment, the display screen 96 can be a television screen of a television.

Figure 9:
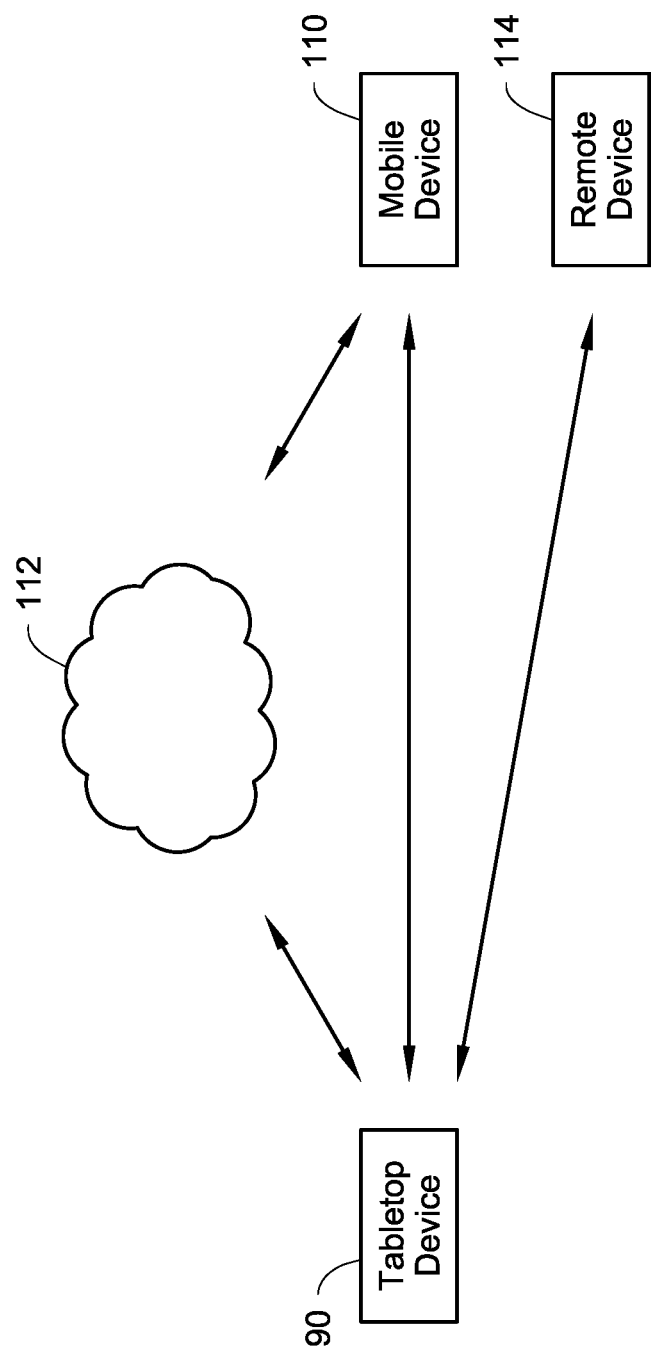
FIG. 9 illustrates a system that incorporates the tabletop device of FIG. 8.

Referring to FIG. 9, a system that incorporates the tabletop device 90 of either FIG. 8 or FIG. 10 is illustrated. In the illustrated system, the tabletop device 90 is in communication, either one-way or two-way communication, with one or more mobile devices 110 and/or with one or more other remote devices 114. The mobile device(s) 110 can be, but is not limited to, the user's mobile device; a parent's mobile device; an aide, nurse, doctor or other medical professional mobile device; or any other mobile device. The mobile device(s) 110 can be a mobile phone, a smartwatch, a tablet device, a laptop computer, and the like. The remote device(s) 114 can be any device that is not a mobile device that is able to interact and communicate with the device 90. For example, the device 114 can be a base station that is designed to interact with the device 90 and that may also interface with another remote device. The device 90 and the mobile device(s) 110 and/or the remote device(s) 114 can communicate with one another via a suitable network 112, for example the internet or other network. In other embodiments, the device 90 and the mobile device(s) 110 and/or the remote device(s) 114 can directly communicate with each other, for example via a suitable short-range wireless communication technique such as Bluetooth®.

In the system of FIG. 9, the results of a reading by the tabletop device 90 can be transmitted, for example in real-time, to the mobile device(s) 110 and/or the remote device(s) 114. For example, the results of the reading by the device 90 can be sent via phone call, email or by text message to the mobile device(s) 110 and/or the remote device(s) 114, or directly via wireless communication. The mobile device(s) 110 and/or the remote device(s) 114 can include an App that is configured to operate with the device 90. In one non-limiting implementation, the system in FIG. 9 permits a reading, for example of an infant or a vulnerable adult, by the device 90 to be sent in real-time to a caregiver's (for example, a parent, aide, nurse, doctor or other medical professional) mobile device 110. If the reading is abnormal, the caregiver can be alerted to that fact allowing the caregiver to render aid or arrange for aid to be rendered. In some embodiments, the signal received by the mobile device(s) 110 and/or the remote device(s) 114 can cause the mobile device(s) 110 and/or the remote device(s) 114 to emit an audible and/or visual alert based on the reading transmitted from the device 90. The mobile device(s) 110 and/or the remote device(s) 114 may also send one or more signals to the device 90. For example, a signal can be sent to the device 90 from the mobile device(s) 110 and/or the remote device(s) 114 after receiving a reading from the device 90 with instructions to the user to take an action or with information relating to the analyte sensed by the sensor. The instructions may be displayed on the display screen 96 of the device 90 and/or the device 90 may audibly present the instructions via the speaker 104.

The interaction between the transmitted signal and the analyte may, in some cases, increase the intensity of the signal(s) that is detected by the receive antenna, and may, in other cases, decrease the intensity of the signal(s) that is detected by the receive antenna. For example, in one non-limiting embodiment, when analyzing the detected response, compounds in the target, including the analyte of interest that is being detected, can absorb some of the transmit signal, with the absorption varying based on the frequency of the transmit signal. The response signal detected by the receive antenna may include drops in intensity at frequencies where compounds in the target, such as the analyte, absorb the transmit signal. The frequencies of absorption are particular to different analytes. The response signal(s) detected by the receive antenna can be analyzed at frequencies that are associated with the analyte of interest to detect the analyte based on drops in the signal intensity corresponding to absorption by the analyte based on whether such drops in signal intensity are observed at frequencies that correspond to the absorption by the analyte of interest. A similar technique can be employed with respect to increases in the intensity of the signal(s) caused by the analyte.

Detection of the presence of the analyte can be achieved, for example, by identifying a change in the signal intensity detected by the receive antenna at a known frequency associated with the analyte. The change may be a decrease in the signal intensity or an increase in the signal intensity depending upon how the transmit signal interacts with the analyte. The known frequency associated with the analyte can be established, for example, through testing of solutions known to contain the analyte. Determination of the amount of the analyte can be achieved, for example, by identifying a magnitude of the change in the signal at the known frequency, for example using a function where the input variable is the magnitude of the change in signal and the output variable is an amount of the analyte. The determination of the amount of the analyte can further be used to determine a concentration, for example based on a known mass or volume of the target. In an embodiment, presence of the analyte and determination of the amount of analyte may both be determined, for example by first identifying the change in the detected signal to detect the presence of the analyte, and then processing the detected signal(s) to identify the magnitude of the change to determine the amount.

The terminology used in this specification is intended to describe particular embodiments and is not intended to be limiting. The terms "a," "an," and "the" include the plural forms as well, unless clearly indicated otherwise. The terms "comprises" and/or "comprising," when used in this specification, specify the presence of the stated features, integers, steps, operations, elements, and/or components, but do not preclude the presence or addition of one or more other features, integers, steps, operations, elements, and/or components.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A non-invasive analyte sensor system, comprising:
a decoupled antenna array having at least one transmit antenna and at least one receive antenna that are decoupled from one another, the at least one transmit antenna is positioned and arranged to transmit a transmit signal into a target containing at least one analyte of interest, and the at least one receive antenna is positioned and arranged to detect a response resulting from transmission of the transmit signal by the at least one transmit antenna into the target containing the at least one analyte of interest;
the at least one transmit antenna has a first geometry and the at least one receive antenna has a second geometry that is geometrically different from the first geometry;
the at least one transmit antenna consists of a strip of conductive material having at least one lateral dimension thereof greater than a thickness dimension thereof; and
the at least one receive antenna consists of a strip of conductive material having at least one lateral dimension thereof greater than a thickness dimension thereof;
the at least one transmit antenna and the at least one receive antenna are arranged side-by-side, and the at least one transmit antenna has a first longitudinal axis and the at least one receive antenna has a second longitudinal axis, and the first longitudinal axis is parallel to the second longitudinal axis;
a transmit circuit that is electrically connectable to the at least one transmit antenna, the transmit circuit is configured to generate a transmit signal to be transmitted by the at least one transmit antenna, the transmit signal is in a radio or microwave frequency range of the electromagnetic spectrum; and
a receive circuit that is electrically connectable to the at least one receive antenna, the receive circuit is configured to receive a response detected by the at least one receive antenna.

2. The non-invasive analyte sensor system of claim 1, wherein the strip of conductive material of the at least one transmit antenna and the strip of conductive material of the at least one receive antenna are disposed on a substrate.

3. The non-invasive analyte sensor system of claim 1, further comprising:

a sensor housing, the decoupled antenna array is attached to the sensor housing, the transmit circuit is disposed in the sensor housing, and the receive circuit is disposed in the sensor housing; and
a battery disposed within the sensor housing, the battery is electrically connected to the decoupled antenna array, the transmit circuit and the receive circuit.

4. The non-invasive analyte sensor system of claim 3, wherein the battery is rechargeable.

5. The non-invasive analyte sensor system of claim 1, wherein the target is human tissue, animal tissue, plant tissue, an inanimate object, soil, a fluid, genetic material, or a microbe.

6. The non-invasive analyte sensor system of claim 1, wherein the at least one analyte of interest comprises blood glucose, blood alcohol, white blood cells, or luteinizing hormone.

7. The non-invasive analyte sensor system of claim 1, wherein the radio or microwave frequency range is between about 10 kHz to about 100 GHz.

8. A tabletop device, comprising:
a housing that includes the non-invasive analyte sensor system of claim 1;
a reading area on the housing at which the at least one transmit antenna and the at least one receive antenna are positioned; and
a trigger mechanism that permits a user to trigger a reading at the reading area.

9. The tabletop device of claim 8, wherein the trigger mechanism comprises a trigger button on the housing, a proximity sensor on the housing, a pressure sensor on the housing, or a voice trigger.

10. A system, comprising:
the tabletop device of claim 8, and a mobile device that is in wireless communication with the tabletop device.

11. A non-invasive analyte sensor system, comprising:
a sensor housing;
a decoupled detector array attached to the sensor housing, the decoupled detector array having at least one transmit element and at least one receive element, the at least one transmit element having a first geometry and the at least one receive element having a second geometry that is geometrically different from the first geometry, the at least one transmit element is positioned and arranged to transmit a transmit signal into a target containing at least one analyte of interest, and the at least one receive element is positioned and arranged to detect a response resulting from transmission of the transmit signal by the at least one transmit element into the target containing the at least one analyte of interest;
the at least one transmit antenna and the at least one receive antenna are arranged side-by-side, and the at least one transmit element has a first longitudinal axis and the at least one receive element has a second longitudinal axis, and the first longitudinal axis is parallel to the second longitudinal axis;
the at least one transmit element consists of a strip of conductive material having at least one lateral dimension thereof greater than a thickness dimension thereof, the strip of conductive material of the at least one transmit element is disposed on a substrate;
the at least one receive element consists of a strip of conductive material having at least one lateral dimension thereof greater than a thickness dimension thereof, the strip of conductive material of the at least one receive element is disposed on a substrate;

a transmit circuit attached to the sensor housing, the transmit circuit is electrically connectable to the at least one transmit element, the transmit circuit is configured to generate a transmit signal to be transmitted by the at least one transmit element, and the transmit signal is in a radio or microwave frequency range of the electromagnetic spectrum; and
a receive circuit attached to the sensor housing, the receive circuit is electrically connectable to the at least one receive element, the receive circuit is configured to receive a response detected by the at least one receive element.

12. The non-invasive analyte sensor system of claim 11, further comprising a battery disposed within the sensor housing, the battery is electrically connected to the decoupled detector array, the transmit circuit and the receive circuit.

13. The non-invasive analyte sensor system of claim 12, wherein the battery is rechargeable.

14. The non-invasive analyte sensor system of claim 11, wherein the target is human tissue, animal tissue, plant tissue, an inanimate object, soil, a fluid, genetic material, or a microbe.

15. The non-invasive analyte sensor system of claim 11, wherein the at least one analyte of interest comprises blood glucose, blood alcohol, white blood cells, or luteinizing hormone.

16. The non-invasive analyte sensor system of claim 11, wherein the radio or microwave frequency range is between about 10 kHz to about 100 GHz.

17. The non-invasive analyte sensor system of claim 11, further comprising:
a reading area on the sensor housing at which the at least one transmit element and the at least one receive element are positioned; and
a trigger mechanism that permits a user to trigger a reading at the reading area.

18. The non-invasive analyte sensor system of claim 17, wherein the trigger mechanism comprises a trigger button on the sensor housing, a proximity sensor on the sensor housing, a pressure sensor on the sensor housing, or a voice trigger.

19. A non-invasive analyte sensor system, comprising:
a sensor housing;
a detector array attached to the sensor housing, the detector array having at least one transmit element and at least one receive element that are decoupled from one another, the at least one transmit element having a first geometry and the at least one receive element having a second geometry that is geometrically different from the first geometry, the at least one transmit element is positioned and arranged to transmit a transmit signal into a target containing at least one analyte of interest, and the at least one receive element is positioned and arranged to detect a response resulting from transmission of the transmit signal by the at least one transmit element into the target containing the at least one analyte of interest;
the at least one transmit element consists of a first strip of conductive material disposed on a substrate, the first strip of conductive material having at least one lateral dimension thereof greater than a thickness dimension thereof;
the at least one receive element consists of a second strip of conductive material disposed on the substrate, the second strip of conductive material having at least one lateral dimension thereof greater than a thickness dimension thereof;

a transmit circuit disposed within the sensor housing, the transmit circuit is electrically connected to the at least one transmit element, the transmit circuit is configured to generate a transmit signal to be transmitted by the at least one transmit element, and the transmit signal has a plurality of different frequencies, each one of the different frequencies is in a range of about 10 kHz to about 100 GHz;

a receive circuit disposed within the sensor housing, the receive circuit is electrically connected to the at least one receive element, the receive circuit is configured to receive a response detected by the at least one receive element; and a rechargeable battery disposed within the sensor housing, the rechargeable battery is electrically connected to the detector array, the transmit circuit and the receive circuit.

20. The non-invasive analyte sensor system of claim 19, wherein the target is human tissue, animal tissue, plant tissue, an inanimate object, soil, a fluid, genetic material, or a microbe.

21. The non-invasive analyte sensor system of claim 19, wherein the at least one analyte of interest comprises blood glucose, blood alcohol, white blood cells, or luteinizing hormone.

22. The non-invasive analyte sensor system of claim 19, further comprising:
   a reading area on the sensor housing at which the at least one transmit element and the at least one receive element are positioned; and
   a trigger mechanism that permits a user to trigger a reading at the reading area.

23. The non-invasive analyte sensor system of claim 22, wherein the trigger mechanism comprises a trigger button on the sensor housing, a proximity sensor on the sensor housing, a pressure sensor on the sensor housing, or a voice trigger.

* * * * *